United States Patent
Shiba et al.

(10) Patent No.: US 11,961,229 B2
(45) Date of Patent: Apr. 16, 2024

(54) OPHTHALMIC IMAGE PROCESSING DEVICE, OCT DEVICE, AND NON-TRANSITORY COMPUTER-READABLE STORAGE MEDIUM

(71) Applicant: NIDEK CO., LTD., Aichi (JP)

(72) Inventors: Ryosuke Shiba, Aichi (JP); Sohei Miyazaki, Aichi (JP); Yusuke Sakashita, Aichi (JP); Yoshiki Kumagai, Aichi (JP); Naoki Takeno, Aichi (JP)

(73) Assignee: NIDEK CO., LTD., Aichi (JP)

( * ) Notice: Subject to any disclaimer, the term of this patent is extended or adjusted under 35 U.S.C. 154(b) by 553 days.

(21) Appl. No.: 17/265,367

(22) PCT Filed: Apr. 15, 2019

(86) PCT No.: PCT/JP2019/016209
§ 371 (c)(1),
(2) Date: Feb. 2, 2021

(87) PCT Pub. No.: WO2020/026535
PCT Pub. Date: Feb. 6, 2020

(65) Prior Publication Data
US 2021/0295508 A1 Sep. 23, 2021

(30) Foreign Application Priority Data
Aug. 3, 2018 (JP) .................................. 2018-147139
Aug. 3, 2018 (JP) .................................. 2018-147141

(51) Int. Cl.
*G06T 7/00* (2017.01)
*A61B 3/10* (2006.01)
*G06T 5/50* (2006.01)

(52) U.S. Cl.
CPC ............ *G06T 7/0012* (2013.01); *A61B 3/102* (2013.01); *G06T 5/50* (2013.01); *G06T 2207/30041* (2013.01)

(58) Field of Classification Search
CPC .............. G06T 7/0012; G06T 5/50; G06T 2207/30041; G06T 2207/20081;
(Continued)

(56) References Cited

U.S. PATENT DOCUMENTS 9,775,508 B1 * 10/2017 Docherty ............. A61B 3/1225
2006/0287850 A1 12/2006 Morikawa
(Continued)

FOREIGN PATENT DOCUMENTS

JP 2009-98970 A 5/2009
JP 2014-505552 A 3/2014
(Continued)

OTHER PUBLICATIONS

Third Party Observation issued Feb. 4, 2022 in Japanese Patent Application No. 2018-147139.
(Continued)

*Primary Examiner* — Lewis G West
(74) *Attorney, Agent, or Firm* — Sughrue Mion, PLLC

(57) ABSTRACT

In this invention, a control unit in an ophthalmic image processing device acquires an ophthalmic image captured by an ophthalmic image capture device (S11). The control unit, by inputting the ophthalmic image into a mathematical model that has been trained by a machine-learning algorithm, acquires a probability distribution in which the random variables are the coordinates at which a specific site and/or a specific boundary of a tissue is present within a region of the ophthalmic image (S14). On the basis of the acquired probability distribution, the control unit detects the specific boundary and/or the specific site (S16, S24).

10 Claims, 14 Drawing Sheets

(58) Field of Classification Search
CPC . G06T 2207/20084; G06T 2207/10101; G06T 7/12; A61B 3/102
See application file for complete search history.

(56) References Cited

U.S. PATENT DOCUMENTS

| | | | |
|---|---|---|---|
| 2011/0190657 A1* | 8/2011 | Zhou | G16H 50/70 600/558 |
| 2012/0194783 A1 | 8/2012 | Wei et al. | |
| 2014/0276025 A1* | 9/2014 | Durbin | A61B 3/0025 600/407 |
| 2015/0062590 A1 | 3/2015 | Bagherinia | |
| 2017/0105616 A1* | 4/2017 | Lowry | A61B 3/1025 |
| 2018/0012359 A1 | 1/2018 | Prentasic et al. | |
| 2018/0144470 A1* | 5/2018 | Govindjee | A61B 5/7267 |
| 2018/0232886 A1 | 8/2018 | Nakagawa et al. | |
| 2020/0211191 A1 | 7/2020 | Joshi | |
| 2020/0245858 A1* | 8/2020 | Takeno | A61B 3/14 |
| 2021/0407096 A1* | 12/2021 | Zangwill | G06T 7/0012 |
| 2022/0164949 A1* | 5/2022 | Shiba | G06N 7/01 |
| 2022/0236580 A1* | 7/2022 | Parrett | G02B 27/48 |

FOREIGN PATENT DOCUMENTS

| | | |
|---|---|---|
| WO | 2005/076258 A1 | 8/2005 |
| WO | 2017/030056 A1 | 2/2017 |
| WO | 2017/070107 A1 | 4/2017 |
| WO | 2018/138564 A1 | 8/2018 |

OTHER PUBLICATIONS

Fang, Leyuan et al., "Automatic segmentation of nine retinal layer boundaries in OCT images of non-exudative AMD patients using deep learning and graph search", Biomedical Optics Express, May 1, 2017, vol. 8, No. 5, pp. 2732-2744. (13 pages total).

Lee, Cecilia S. et al., "Deep-learning based, automated segmentation of macular edema in optical coherence tomography", Biomedical Optics Express, Jul. 1, 2017, vol. 8, No. 7, pp. 3440-3448. (9 pages total).

He, Yufan et al., "Topology guaranteed segmentation of the human retina from OCT using convolutional neural networks", arXiv:1803.05120v1 [cs.CV], Mar. 14, 2018. (9 pages total).

Schlegl, Thomas et al., "Unsupervised Anomaly Detection with Generative Adversarial Networks to Guide Marker Discovery", arXiv:1703.05921v1 [cs.CV], Mar. 17, 2017. (12 pages total).

Devalla, Sripad Krishna et al., "A Deep Learning Approach to Digitally Stain Optical Coherence Tomography Images of the Optic Nerve Head", Investigative Ophthalmology & Visual Science, Jan. 10, 2018, vol. 59, No. 1, pp. 63-74.

Shiihara, Hideki et al., "Attempt at Automatic Stratification of Choroidal En face Images by Machine Learning", Journal of Japanese Ophthalmological Society, Mar. 9, 2018, vol. 122 special extra edition. (6 pages total).

International Search Report (PCT/ISA/210) dated Jun. 25, 2019 by the International Searching Authority in counterpart International Patent Application No. PCT/JP2019/016209.

Written Opinion (PCT/ISA/237) dated Jun. 25, 2019 by the International Searching Authority in counterpart International Patent Application No. PCT/JP2019/016209.

Communication dated Jul. 26, 2022 by the Japanese Patent Office in Japanese Patent Application No. 2018-147141.

Communication dated Mar. 25, 2022 issued by the European Patent Office in application No. 19843402.9.

Koozekanani, D., et al., "Retinal Thickness Measurements from Optical Coherence Tomography Using a Markov Boundary Model", IEEE Transactions on Medical Imaging, vol. 20, No. 9, Sep. 2001, pp. 900-916.

Roy, A., et al., "ReLayNet: Retinal Layer and Fluid Segmentation of Macular Optical Coherence Tomography using Fully Convolutional Network", arXiv: 1704.02161v1 [cs.CV], Apr. 7, 2017, pp. 1-24.

Kafieh, R., et al., "A Review of Algorithms for Segmentation of Optical Coherence Tomography from Retina", Journal of Medical Signals & Sensors, vol. 3, Issue 1, Jan. 1, 2013, pp. 45-60 (17 pages).

DeBuc, D., et al. "A Review of Algorithms for Segmentation of Retinal Image Data Using Optical Coherence Tomography", Image Segmentation, Apr. 19, 2011, pp. 15-54 (41 pages).

Ngo, L., et al., "Deep Neural Network Regression for Automated Retinal Layer Segmentation in Optical Coherence Tomography Images", IEEE Transactions on Image Processing, vol. 29, Aug. 1, 2019, pp. 303-312.

Notification of Reasons for Refusal issued Dec. 19, 2023 by the Japan Patent Office in counterpart Japanese Patent Application No. 2022-204040.

* cited by examiner

FIG. 15
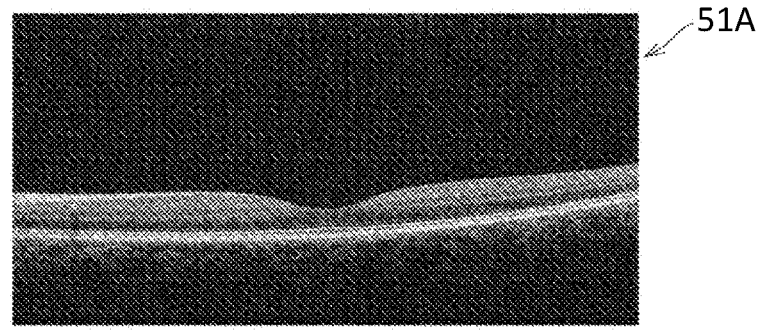
AVERAGE ENTROPY
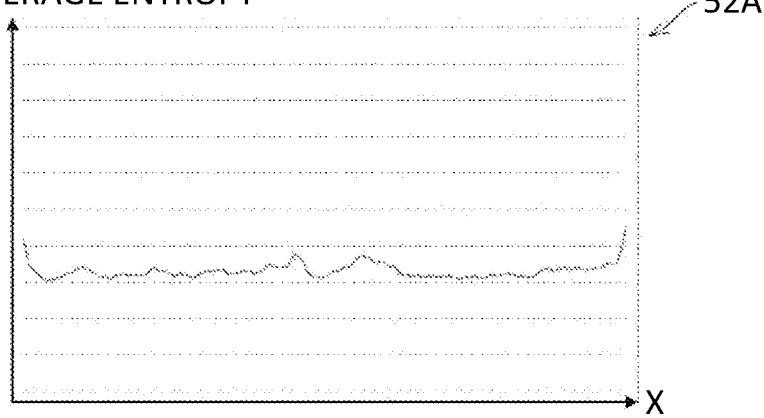
| BOUNDARY | ENTROPY |
|---|---|
| ILM | 1.19 |
| NFL/GCL | 1.90 |
| IPL/INL | 2.57 |
| OPL/ONL | 2.60 |
| IS/OS | 1.52 |
| RPE/BM | 1.52 |
| AVERAGE OF ALL BOUNDARIES | 1.88 |
| AVERAGE OF IPL/INL AND OPL/ONL | 2.59 |

FIG. 16
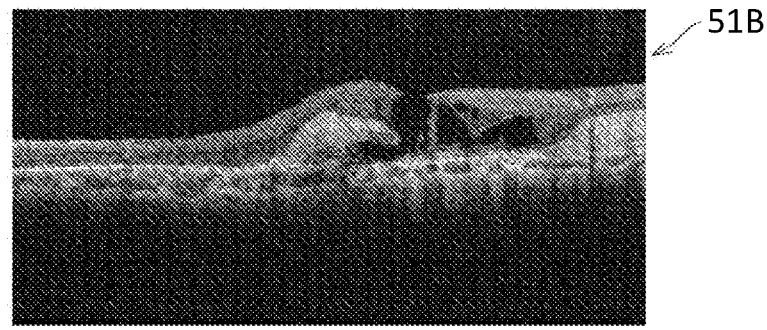
AVERAGE ENTROPY
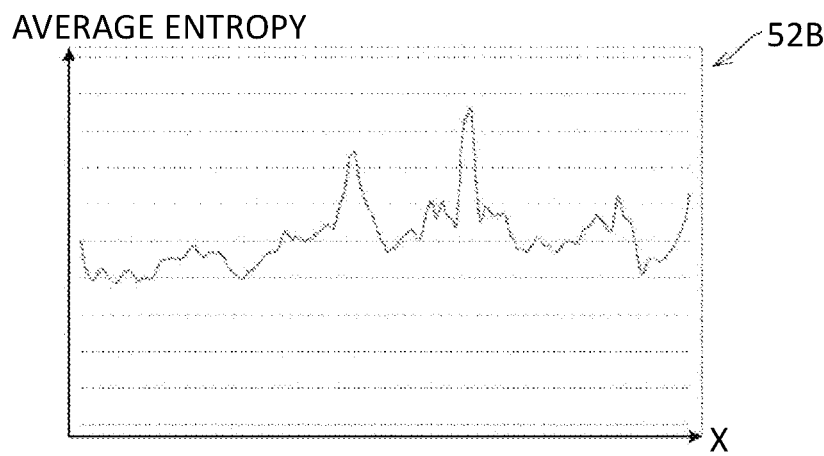
| BOUNDARY | ENTROPY |
|---|---|
| ILM | 1.55 |
| NFL/GCL | 2.77 |
| IPL/INL | 3.73 |
| OPL/ONL | 3.80 |
| IS/OS | 3.47 |
| RPE/BM | 2.71 |
| AVERAGE OF ALL BOUNDARIES | 3.01 |
| AVERAGE OF IPL/INL AND OPL/ONL | 3.77 |
51B
52B
53B

OPHTHALMIC IMAGE PROCESSING DEVICE, OCT DEVICE, AND NON-TRANSITORY COMPUTER-READABLE STORAGE MEDIUM

CROSS-REFERENCE TO RELATED APPLICATIONS

This application is a National Phase Entry of PCT International Application No. PCT/JP2019/016209 filed on Apr. 15, 2019, which claims priority to Japanese Patent Application Nos. 2018-147139 filed on Aug. 3, 2018 and 2018-147141 filed on Aug. 3, 2018, the entire contents of which are incorporated by reference herein.

TECHNICAL FIELD

The present disclosure relates to an ophthalmic image processing device that processes an ophthalmic image of a subject eye, an OCT device, and a non-transitory computer-readable storage medium storing an ophthalmic image processing program that is executed in the ophthalmic image processing device.

BACKGROUND ART

In the related art, various techniques have been proposed for detecting at least one of a boundary of a plurality of tissues (for example, a plurality of layers) shown in an ophthalmic image and a specific part on a tissue shown in an ophthalmic image (hereinafter, it may be simply referred to as "boundary/specific part"). For example, in the technique disclosed in Non-Patent Literature 1, first, which layer each pixel belongs to is mapped for each pixel. Next, the boundary of each layer is detected by outputting the thickness of each layer based on the mapping result.

As another example, various techniques for estimating abnormality in a structure of an object shown in an image or the like have been proposed. For example, in the technique disclosed in Non-Patent Literature 2, first, using normal images as training data Generative Adversarial Network (GAN) is trained. The trained GAN learns to map the input image to coordinates on a latent space. When there is an abnormality in the structure of the input image or the like, a difference occurs between an image generated by the mapping and the input image. In the technique of Non-Patent Literature 2, an attempt is made to estimate an abnormal part of a structure by taking a difference between an image generated by mapping and an input image.

CITATION LIST

Non-Patent Literature

Non-Patent Literature 1: Yufan He, Aaron Carass, et al. "Topology guaranteed segmentation of the human retina from OCT using convolutional neural networks." arXiv: 1803.05120, 14 Mar. 2018

Non-Patent Literature 2: Thomas Schlegl, et al. "Unsupervised Anomaly Detection with Generative Adversarial Networks to Guide Marker Discovery" arXiv: 1703.05921, 17 Mar. 2017

SUMMARY OF INVENTION

In the method in Non-Patent Literature 1, for example, when the structure of the tissue is collapsed due to the influence of a disease, it becomes difficult to accurately map which tissue each pixel belongs to. As a result, the detection accuracy of the boundary/specific part of the tissue is also reduced.

In the method of Non-Patent Literature 2, since the attempt is being made to estimate the abnormal part by taking the difference between the image generated by the mapping and the input image, it is difficult to quantify the degree of abnormality in the structure. Therefore, it is difficult for a user to appropriately determine the abnormality of the structure of a tissue shown in an ophthalmic image.

One typical object of the present disclosure is to provide an ophthalmic image processing device, an OCT device, and a non-transitory computer-readable storage medium storing an ophthalmic image processing program capable of appropriately detecting at least one of a boundary and a specific part of a tissue shown in an ophthalmic image.

Another typical object of the present disclosure is to provide an ophthalmic image processing device, an OCT device, and a non-transitory computer-readable storage medium storing an ophthalmic image processing program capable of appropriately determining an abnormality in the structure of a tissue shown in an ophthalmic image by a user.

According to a first aspect of the typical embodiment in the present disclosure, there is provided an ophthalmic image processing device that processes an ophthalmic image which is an image of a tissue of a subject eye, including:
a controller configured to:
acquire an ophthalmic image captured by an ophthalmic image capturing device;
acquire a probability distribution, in which a coordinate is a random variable and in which at least one of a specific boundary and a specific part of the tissue exists inside a region in the ophthalmic image, by inputting the ophthalmic image into a mathematical model trained with using a machine learning algorithm; and
detect at least one of the specific boundary and the specific part based on the acquired probability distribution.

According to a second aspect of the typical embodiment in the present disclosure, there is provided an OCT device that captures an ophthalmic image of a tissue of a subject eye by processing an OCT signal derived from reference light and reflected light of measurement light with which the tissue is irradiated, including:
a controller configured to:
acquire a probability distribution, in which a coordinate is a random variable and in which at least one of a specific boundary and a specific part of the tissue exists inside a region in the ophthalmic image, by inputting the captured ophthalmic image into a mathematical model trained with using a machine learning algorithm; and
detect at least one of the specific boundary and the specific part based on the acquired probability distribution.

According to a third aspect of the typical embodiment in the present disclosure, there is provided a non-transitory computer-readable storage medium storing an ophthalmic image processing program executed by an ophthalmic image processing device that processes an ophthalmic image which is an image of a tissue of a subject eye, the program being executed by a controller of the ophthalmic image processing device to cause the ophthalmic image processing device to execute:

an image acquisition step of acquiring an ophthalmic image captured by an ophthalmic image capturing device;

a probability distribution acquisition step of acquiring a probability distribution, in which a coordinate is a random variable and in which at least one of a specific boundary and a specific part of the tissue exists inside a region in the ophthalmic image, by inputting the ophthalmic image into a mathematical model trained with using a machine learning algorithm; and a detection step of detecting at least one of the specific boundary and the specific part based on the acquired probability distribution.

According to the ophthalmic image processing device of the first aspect, the OCT device of the second aspect, and the non-transitory computer-readable storage medium storing the ophthalmic image processing program of the third aspect, at least one of the boundary and the specific part of the tissue shown in the ophthalmic image is appropriately detected.

According to a fourth aspect of the typical embodiment in the present disclosure, there is provided an ophthalmic image processing device that processes an ophthalmic image which is an image of a tissue of a subject eye, including:

a controller configured to:
acquire an ophthalmic image captured by an ophthalmic image capturing device;
acquire a probability distribution for identifying a tissue in the ophthalmic image by inputting the ophthalmic image into a mathematical model trained with using a machine learning algorithm; and
acquire a degree of divergence of the acquired probability distribution with respect to the probability distribution acquired in a case where the tissue is accurately identified, as structural information indicating a degree of abnormality in a structure of the tissue.

According to a fifth aspect of the typical embodiment in the present disclosure, there is provided an OCT device that captures an ophthalmic image of a tissue of a subject eye by processing an OCT signal derived from reference light and reflected light of measurement light with which the tissue is irradiated, including:

a controller configured to:
acquire a probability distribution for identifying a tissue in the ophthalmic image by inputting the captured ophthalmic image into a mathematical model trained with using a machine learning algorithm; and
acquire a degree of divergence of the acquired probability distribution with respect to the probability distribution acquired in a case where the tissue is accurately identified, as structural information indicating a degree of abnormality in a structure of the tissue.

According to a sixth aspect of the typical embodiment in the present disclosure, there is provided a non-transitory computer-readable storage medium storing an ophthalmic image processing program executed by an ophthalmic image processing device that processes an ophthalmic image which is an image of a tissue of a subject eye, the program being executed by a controller of the ophthalmic image processing device to cause the ophthalmic image processing device to execute:

an image acquisition step of acquiring an ophthalmic image captured by an ophthalmic image capturing device;

a probability distribution acquisition step of acquiring a probability distribution for identifying a tissue in the ophthalmic image by inputting the ophthalmic image into a mathematical model trained with using a machine learning algorithm; and a structural information acquisition step of acquiring a degree of divergence of the acquired probability distribution with respect to the probability distribution acquired in a case where the tissue is accurately identified, as structural information indicating a degree of abnormality in a structure of the tissue.

According to the ophthalmic image processing device of the fourth aspect, the OCT device of the fifth aspect, and the non-transitory computer-readable storage medium storing the ophthalmic image processing program of the sixth aspect, it is possible for a user to appropriately determine the abnormality of the tissue shown in the ophthalmic image.

BRIEF DESCRIPTION OF DRAWINGS

FIG. 15 is an example of a display screen on which a two-dimensional tomographic image 51A, a degree of structural abnormality graph 52A, and a degree of divergence table 53A are displayed.

FIG. 16 is an example of a display screen on which a two-dimensional tomographic image SIB, a degree of structural abnormality graph 52B, and a degree of divergence table 53B are displayed.

DESCRIPTION OF EMBODIMENTS

<Outline>

Figure 1:
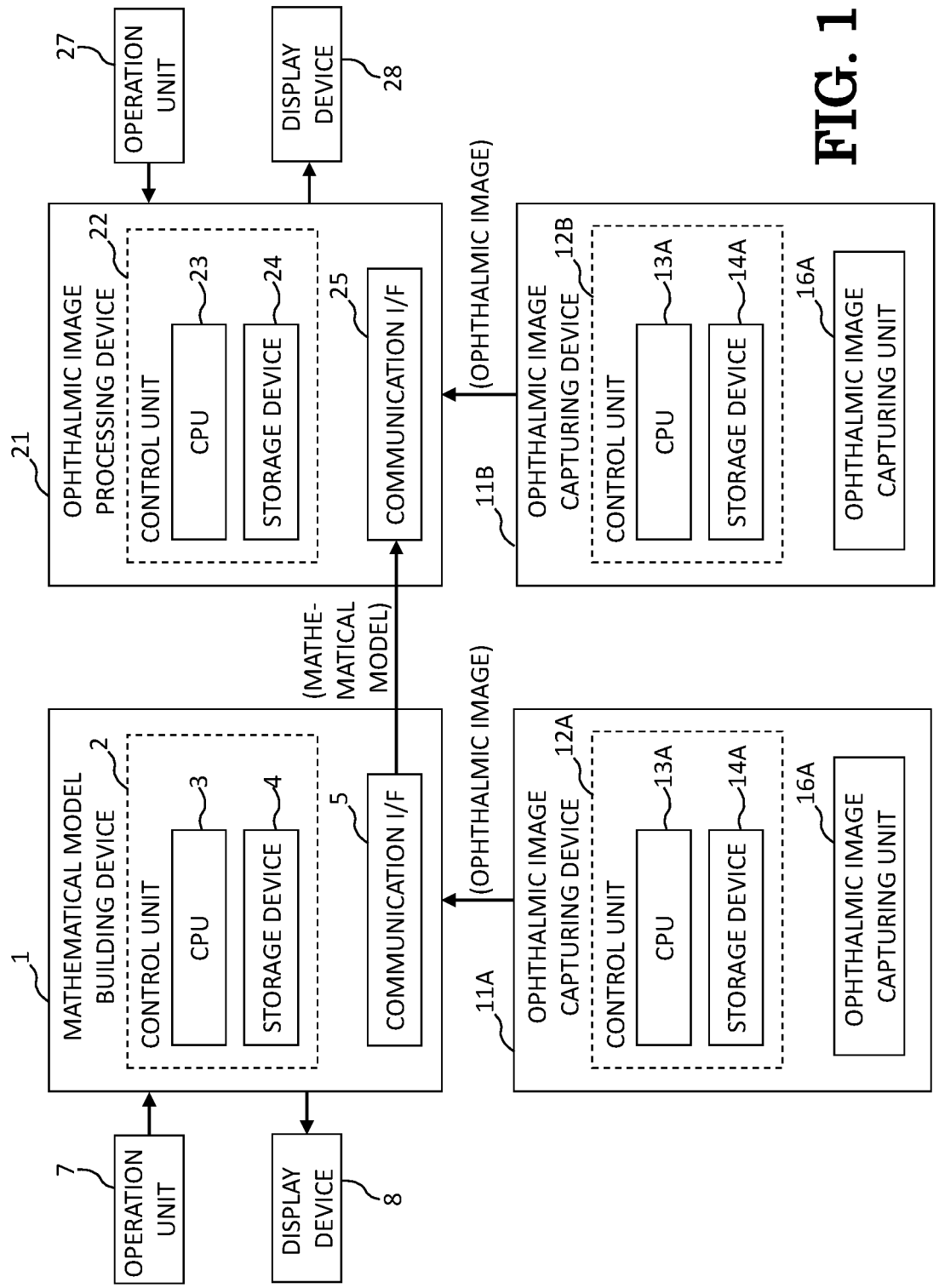
FIG. 1 is a block diagram illustrating a schematic configuration of a mathematical model building device 1, an ophthalmic image processing device 21, and an ophthalmic image capturing devices 11A and 11B.

A controller of an ophthalmic image processing device exemplified in the example of the present disclosure acquires an ophthalmic image captured by the ophthalmic image capturing device. By inputting the ophthalmic image into a mathematical model trained with using a machine learning algorithm, the controller acquires a probability distribution, in which a coordinate is a random variable, and in which at least one of a specific boundary and a specific part of a tissue exists in a region in the ophthalmic image. The controller detects at least one of the specific boundary and the specific part based on the acquired probability distribution.

According to the ophthalmic image processing device exemplified in the example of the present disclosure, even when a structure of the tissue is collapsed due to an influence of a disease, or image quality of at least a part of the ophthalmic image is not good, the boundary/specific part is detected appropriately and directly based on the probability distribution of the random variable on the coordinate.

Note that in the above-mentioned example of the related art, after mapping which layer each pixel belongs to, the thickness of the layer is output based on the mapping result, and finally the boundary of the layer is detected. In this case, it is difficult to reduce the amount of processing because multi-stage processing is required. In contrast to this, in the ophthalmic image processing device illustrated in the example of the present disclosure, the amount of processing for detecting the boundary/specific part based on the probability distribution of the random variable on the coordinate is small. Therefore, the amount of processing tends to be reduced easily.

Note that the above-mentioned "region" may be any one of a region of one-dimension, a region of two-dimensions, and a region of three-dimensions. When the "region" is the region of one-dimension, the coordinate is a one-dimensional coordinate. Similarly, when the "region" is the region of two-dimensions, the coordinate is two-dimensional coordinates, and when the "region" is the region of three-dimensions, the coordinate is three-dimensional coordinates.

Note that the "specific boundary" that is a target for acquiring the probability distribution may be one boundary or a plurality of boundaries. When acquiring the probability distribution of a plurality of boundaries, the controller may acquire the probability distributions of each of the plurality of boundaries separately. Similarly, the number of parts of the "specific parts" that are targets for acquiring the probability distribution may be one or plural.

The mathematical model may be used in the processing of detecting the boundary/specific part based on the probability distribution in the same manner as in the processing of acquiring the probability distribution. Further, the controller itself may detect the boundary/specific part based on the acquired probability distribution without using the mathematical model.

The mathematical model may be trained with using a training data set in which data of the ophthalmic image of the tissue of a subject eye that is captured ago is used for an input side, and data indicating at least one position of the specific boundary and the specific part of the tissue in the ophthalmic image of the input side is used for an output side. In this case, the trained mathematical model can appropriately output the probability distribution of the specific boundary/specific part, in which the coordinate is a random variable, by inputting the ophthalmic image.

Note that the mathematical model building method executed by the mathematical model building device for building the mathematical model can be expressed as follows. A mathematical model building method executed by a mathematical model building device that builds a mathematical model, which is built by being trained with using a machine learning algorithm and outputs data according to the input ophthalmic image by inputting an ophthalmic image, the method including: an output training data acquisition step of acquiring the ophthalmic image of a tissue of a subject eye as a training ophthalmic image, an output training data acquisition step of acquiring training data indicating at least one position of a specific boundary and a specific part of the tissue in the training ophthalmic image acquired in the input training data acquisition step: and a training step of building the mathematical model that outputs a probability distribution, in which a coordinate is a random variable, and in which at least one of the specific boundary and the specific part of the tissue exists inside the region in the input ophthalmic image, by training the mathematical model with using the training ophthalmic image data as input training data and with using the training data as output training data.

By inputting the ophthalmic image into the mathematical model, the controller may acquire the probability distribution, in which the one-dimensional coordinate is a random variable, and in which the specific boundary exists in a one-dimensional region extending in a direction intersecting the specific boundary of the tissue in the ophthalmic image. The controller may detect the specific boundary based on the acquired probability distribution. In this case, since it is easy to obtain the appropriately biased probability distribution, it is easy to improve the detection accuracy of the specific boundary.

Note that the ophthalmic image may be a two-dimensional tomographic image or a three-dimensional tomographic image captured by an OCT device. In this case, a probability distribution of a random variable on a one-dimensional coordinate may be acquired for the one-dimensional region extending in the direction of the optical axis of the measurement light made by the OCT device (so-called an "A-scan direction"). The direction of the boundary of the tissue tends to be close to perpendicular with respect to the A-scan direction. Therefore, by setting a direction in which the one-dimensional region extends as the A-scan direction, the probability distribution tends to be appropriately biased. Further, it reduces the possibility of two or more intersections of a one-dimensional region and the specific boundary. Therefore, the detection accuracy of the specific boundary is improved. Further, the controller may acquire the probability distribution of the random variable on the one-dimensional coordinate for the one-dimensional region extending perpendicularly with respect to the specific boundary. In this case, the probability distribution tends to be more biased.

The controller may detect a two-dimensional or three-dimensional boundary based on a plurality of probability distributions acquired for each of a plurality of one-dimensional regions different from each other. In this case, the two-dimensional or three-dimensional boundary is appropriately recognized.

Note that the two-dimensional or three-dimensional boundary may be detected after post-processing is performed with respect to the probability distribution related to each of the plurality of one-dimensional regions. For example, a boundary on the N-th one-dimensional region may be detected based on the probability distribution on the N-th one-dimensional region and the probability distribution on the one-dimensional region positioned in the vicinity of the N-th one-dimensional region. In this case, for example, a known method such as a graph cut can be adopted. Further, the two-dimensional or three-dimensional boundary may be detected by using the theory of the shortest path search for finding the path having the minimum weight.

The controller may acquire a two-dimensional or three-dimensional map showing a specific boundary-likeness, which is generated based on the plurality of probability distributions acquired for each of the plurality of one-dimensional regions. That is, the ophthalmic image processing device may execute a map acquisition step of acquiring the two-dimensional or three-dimensional map showing the specific boundary-likeness. In this case, a position of the two-dimensional or three-dimensional specific boundary is appropriately recognized based on the map.

Note that the controller may display the acquired map on the display device. In this case, the user can appropriately recognize the position of the two-dimensional or three-dimensional specific boundary by looking at the displayed map. The map may be generated by the controller based on the plurality of probability distributions output from the mathematical model. Further, the mathematical model may output the map.

The ophthalmic image may be a three-dimensional tomographic image captured by the OCT device. Based on the three-dimensional tomographic image and the detected three-dimensional boundary, the controller may acquire a two-dimensional front image (so-called "Enface image") at a sight of a specific layer included in the three-dimensional tomographic image from a direction along the optical axis of the measurement light. That is, the ophthalmic image processing device may execute an Enface image acquisition step of acquiring the Enface image based on the three-dimensional tomographic image and the detected three-dimensional boundary. In this case, after the specific layer is specified based on the appropriately detected boundary, the Enface image of the specific layer is appropriately acquired. The Enface image may be generated by the controller. Further, the mathematical model may output an Enface image.

Further, the controller may acquire a thickness map showing the distribution of the thickness of a specific layer included in the three-dimensional tomographic image in two dimensions based on the three-dimensional tomographic image and the detected three-dimensional boundary. In this case, the specific layer is specified based on the appropriately detected boundary, and a more accurate thickness map is acquired.

By inputting the ophthalmic image into the mathematical model, the controller may acquire the probability distribution of a probability that the specific part may exist in the two or more dimensions region of the ophthalmic image, in which the coordinates of the two or more dimensions are random variables. The controller may detect the specific part based on the acquired probability distribution. In this case, the specific part is appropriately detected in the two-dimensional region or the three-dimensional region.

A controller of an ophthalmic image processing device exemplified in another example of the present disclosure acquires an ophthalmic image captured by the ophthalmic image capturing device. By inputting the ophthalmic image into the mathematical model trained with using the machine learning algorithm, the controller acquires a probability distribution for identifying the tissue in the ophthalmic image. The controller acquires the degree of divergence of the acquired probability distribution with respect to the probability distribution acquired in a case where the tissue is accurately identified as structural information indicating the degree of abnormality in the structure of the tissue.

In another example of the present disclosure, when there is no abnormality in the structure of the tissue, the tissue tends to be identified accurately by the mathematical model, so that the probability distribution to be acquired tends to be biased. On the other hand, when there is an abnormality in the structure of the tissue, the acquired probability distribution is less likely to be biased. Therefore, the degree of divergence between the probability distribution acquired in the case where the tissue is accurately identified and the actually acquired probability distribution increases or decreases according to the degree of abnormality in the structure. Therefore, according to the ophthalmic image processing device of another example of the present disclosure, the degree of abnormality in the structure is appropriately quantified by the degree of divergence. Further, when training the mathematical model, the degree of abnormality in the structure of the tissue can be recognized by the degree of divergence without using a large number of ophthalmic images of the tissue in which the abnormality exists. Therefore, the user can appropriately determine the abnormality of the structure of the tissue shown in the ophthalmic image.

Note that the degree of divergence may be output by the mathematical model. Further, the controller may calculate the degree of divergence based on the probability distribution output by the mathematical model.

In another example of the present disclosure, the mathematical model may be trained with using a training data set in which data of the ophthalmic image of the tissue of the subject eye that is captured ago is used for the input side, and data indicating the tissue in the ophthalmic image of the input side is used for the output side. In this case, the trained mathematical model can appropriately output the probability distribution for identifying the tissue by inputting the ophthalmic image.

Note that in another example of the present disclosure, a specific aspect of the mathematical model that outputs the probability distribution can be appropriately selected. For example, the mathematical model may output the probability distribution, in which a coordinate is a random variable, and in which at least one of the specific boundary and the specific part of the tissue exists inside the region in the input ophthalmic image. In this case, the tissue in the ophthalmic image (in this case, at least one of the boundary and the specific part) is appropriately and directly identified based on the probability distribution output by the mathematical model. Note that in this case, the "specific boundary" that is a target for acquiring the probability distribution may be one boundary or a plurality of boundaries. When acquiring the probability distribution of a plurality of boundaries, the controller may acquire the probability distributions of each of the plurality of boundaries separately. Similarly, the number of parts of the "specific parts" that are targets for acquiring the probability distribution may be one or plural. Further, the region in the ophthalmic image as a unit for acquiring the probability distribution may be any of a one-dimensional region, a two-dimensional region, and a three-dimensional region. The dimension of the coordinate which is a random variable may match the dimension of the region that is the unit for acquiring the probability distribution. Further, the mathematical model may output the probability distribution in which the type of each tissue in the subject eye is a random variable, for each region (for example, for each pixel) of the input ophthalmic image. Even in this case, the tissue in the ophthalmic image is identified based on the probability distribution output by the mathematical model.

The degree of divergence may include the entropy (the average amount of information) of the acquired probability distribution. The entropy represents the degree of uncertainty, messiness, and disorder. In the present disclosure, the entropy of the probability distribution output in the case where the tissue is accurately identified is zero. Further, the entropy increases as the degree of abnormality in the structure of the tissue increases and it becomes difficult to identify the tissue. Therefore, by using the entropy of the probability distribution as the degree of divergence, the degree of abnormality in the structure of the tissue is more appropriately quantified.

However, a value other than entropy may be adopted as the degree of divergence. For example, at least one of the standard deviation, the coefficient of variation, the variance, and the like indicating the degree of dispersion of the acquired probability distribution may be used as the degree of divergence. The KL divergence or the like, which is a measure for measuring the difference between probability distributions, may be used as the degree of divergence. Further, the maximum value of the acquired probability distribution may be used as the degree of divergence.

In another example of the present disclosure, the ophthalmic image may be a two-dimensional tomographic image or a three-dimensional tomographic image of the tissue. By inputting the ophthalmic image into the mathematical model, the controller may acquire the probability distribution for identifying one or more layers or boundaries included in a plurality of layers and boundaries of the layers in the ophthalmic image. The controller may acquire the degree of divergence for the one or more layers or boundaries. In this case, the degree of abnormality in the structure of the specific layer or the boundary is appropriately recognized by the degree of divergence. For example, when only the degree of divergence of the layer or boundary where the abnormality in the structure is likely to occur due to the influence of the disease is acquired, the acquired degree of divergence can be more useful information related to the disease.

In another example of the present disclosure, the controller may acquire at least one of a graph and a map showing the magnitude of the degree of divergence with respect to the position in the tissue. The user can appropriately recognize which position in the tissue has a higher degree of abnormality by at least one of the graph and the map.

In another example of the present disclosure, for example, the ophthalmic image may be a two-dimensional image spreading in the XZ direction. By inputting the ophthalmic image into the mathematical model, the controller may acquire the probability distribution of the random variable on the one-dimensional coordinate for each of a plurality of one-dimensional regions extending parallel to the Z direction on the ophthalmic image and may acquire the degree of divergence for each of the plurality of one-dimensional regions. The controller may acquire a degree of structural abnormality graph showing the magnitude of the degree of divergence at each position in the X direction based on the degree of divergence acquired for each of the plurality of one-dimensional regions. In this case, the user can appropriately recognize which position of the two-dimensional ophthalmic image in the X direction has a high degree of abnormality from the degree of structural abnormality graph.

In this case, the two-dimensional image may be the two-dimensional tomographic image of the tissue or the two-dimensional front image of the tissue. In the case of the two-dimensional tomographic image, the degree of divergence acquired for each of the plurality of one-dimensional regions may be acquired for each layer or boundary or may be acquired as an average value of a plurality of layers and boundaries. Note that the degree of structural abnormality graph may be output by the mathematical model. Further, the controller may generate the degree of structural abnormality graph based on the degree of divergence acquired for each of a plurality of axes. The controller may display the acquired degree of structural abnormality graph on the display device.

Further, in another example of the present disclosure, the controller may acquire a degree of structural abnormality map showing the two-dimensional distribution of the degree of divergence in the tissue. In this case, the user can accurately recognize the degree of abnormality in the structure at each position in the two-dimensional region by the degree of structural abnormality map. Note that the degree of structural abnormality map may be output by the mathematical model. Further, the controller may generate the degree of structural abnormality map based on the acquired degree of divergence. The controller may display the acquired degree of structural abnormality map on the display device.

Note that in another example of the present disclosure, it is also possible to allow the user to recognize the degree of abnormality in the structure of the tissue without using the graph and the map. For example, the controller may notify the user of the acquired degree of divergence itself as structural information indicating the degree of abnormality in the structure.

In another example of the present disclosure, the controller may execute processing of outputting an imaging instruction for imaging a part of the tissue having the degree of divergence equal to or higher than a threshold value to the ophthalmic image capturing device. Further, the controller may execute processing of displaying a tomographic image or an enlarged image of the part having the degree of divergence equal to or higher than the threshold value on the display device. In this case, the image of the part having a high degree of abnormality in the structure is appropriately checked by the user.

Note that in another example of the present disclosure, when the controller outputs the imaging instruction for imaging the part having the degree of divergence equal to or higher than the threshold value, the controller may capture the ophthalmic image of the part having the degree of divergence equal to or higher than the threshold value a plurality of times, and output the instruction for acquiring an average added image of the plurality of captured ophthalmic images. In this case, the ophthalmic image of the part having a high degree of abnormality in the structure is acquired with high quality.

In another example of the present disclosure, of the plurality of ophthalmic images captured the an identical tissue of the subject eye, the controller may display an ophthalmic image having the highest degree of divergence or an ophthalmic image having the degree of divergence equal to or higher than the threshold value on the display device. For example, by displaying the ophthalmic image having a high degree of divergence of the plurality of ophthalmic images on a capture checking screen that allows the user to check the captured ophthalmic image, the controller can easily allow the user to check the ophthalmic image obtained by imaging the part having a high degree of abnormality in the structure. Further, by displaying the ophthalmic image having a high degree of divergence of the plurality of ophthalmic images when a viewer is activated to allow the user to check the captured ophthalmic image, the controller can first allow the user to check the ophthalmic image obtained by imaging the part having a high degree of abnormality in the structure.

In another example of the present disclosure, of the plurality of two-dimensional tomographic images that constitute the three-dimensional tomographic image, the controller may input the two-dimensional tomographic image having the highest degree of divergence or the two-dimensional tomographic image having the degree of divergence equal to or higher than the threshold value into the mathematical model that outputs an automatic diagnosis result related to the disease of the subject eye. In this case, the efficient automatic diagnosis result can be obtained by using the two-dimensional tomographic image having a high degree of abnormality in the structure of the plurality of two-dimensional tomographic images that constitute the three-dimensional tomographic image.

In another example of the present disclosure, the controller may store the acquired degree of divergence in the storage device. The controller may display a plurality of degrees of divergence for each of the plurality of ophthalmic images obtained by capturing an identical tissue of the subject eye at different times on the display device. In this case, the user can appropriately recognize the progress of the abnormality in the structure and the like by comparing the plurality of degrees of divergence. Note that the controller may display the plurality of values of the degree of divergence or display a plurality of the above described degree of structural abnormality graphs side by side. Further, the controller may display a plurality of the above described degree of structural abnormality maps side by side.

In another example of the present disclosure, the controller may generate image quality evaluation information for evaluating the image quality of the ophthalmic image based on the degree of divergence acquired for the ophthalmic image. The degree of divergence may be high not only when there is an abnormality in the structure of the tissue but also when the image quality of the ophthalmic image is poor. Therefore, the image quality of the ophthalmic image can be appropriately recognized by generating the image quality evaluation information based on the degree of divergence.

Note that the specific method for generating the image quality evaluation information can be appropriately selected. For example, the value of the degree of divergence itself may be used as the image quality evaluation information. Further, when there is an abnormality in a part of the structure of the tissue, the degree of divergence of the part having abnormality becomes higher than the degree of divergence of the other part. On the other hand, when the image quality is poor, the degree of divergence of each part of the ophthalmic image becomes high as a whole. Therefore, when the degree of divergence is acquired for each part of the ophthalmic image, the controller may generate image quality evaluation information indicating that the image quality is poor when all the degree of divergence of each part are high (for example, when all the degree of divergence of each part are equal to or higher than the threshold value). Further, the controller may generate image quality evaluation information in consideration of the strength of a signal of the captured ophthalmic image or an index indicating the goodness of the signal (for example, SSI (Signal Strength Index) or QI (Quality Index), or the like), and the acquired degree of divergence.

Further, in another example of the present disclosure, the controller may generate information indicating the degree of abnormality in the structure of the tissue based on the index indicating the signal strength or goodness of the ophthalmic image and the acquired degree of divergence. For example, the controller may generate information indicating that there is a high possibility that an abnormality exists in the structure when the index of the signal of the image is equal to or higher than the threshold value and the degree of divergence is equal to or higher than the threshold value. In this case, the abnormality in the structure is determined more appropriately after considering the image quality of the ophthalmic image.

Note that it is also possible to use the degree of divergence as the image quality evaluation information without using the degree of divergence as the structural information indicating the degree of abnormality in the structure of the tissue. In this case, the ophthalmic image processing device can be expressed as follows. An ophthalmic image processing device that processes an ophthalmic image that is an image of a tissue of a subject eye, in which the controller of the ophthalmic image processing device acquires the ophthalmic image captured by an ophthalmic image capturing device, acquires a probability distribution for identifying the tissue in the ophthalmic image by inputting the ophthalmic image into a mathematical model trained with using a machine learning algorithm, and acquires a degree of divergence of the acquired probability distribution with respect to the probability distribution acquired in the case where the tissue is accurately identified, as image quality evaluation information for evaluating image quality of the ophthalmic image.

Note that in the present disclosure, various images can be used as the ophthalmic images input into the mathematical model. For example, the ophthalmic image may be the two-dimensional tomographic image or the three-dimensional tomographic image of the tissue of the subject eye captured by an OCT device. The tomographic image may be captured by a device other than the OCT device (for example, a shine-proof camera or the like). Further, the ophthalmic image may be a two-dimensional front image captured by a fundus camera, a two-dimensional front image captured by a scanning laser ophthalmoscopy (SLO), or the like. The ophthalmic image may be a two-dimensional front image (so-called "Enface image") generated based on the data of the three-dimensional tomographic image captured by the OCT device. Further, the ophthalmic image may be a two-dimensional front image (so-called "motion contrast image") created from the motion contrast data obtained by processing a plurality of OCT data acquired from the same position at different times. The two-dimensional front image is a two-dimensional image obtained by capturing the tissue from the direction of the optical axis of the imaging light. Further, the tissue that is an imaging target can be appropriately selected. For example, an image obtained by capturing any of the fundus, anterior segment, angle, or the like of the subject eye may be used as the ophthalmic image.

Embodiment (Device Configuration)

Hereinafter, a typical embodiment in the present disclosure will be described with reference to the drawings. As illustrated in FIG. 1, in the present embodiment, a mathematical model building device 1, an ophthalmic image processing device 21, and an ophthalmic image capturing devices 11A and 11B are used. The ophthalmic image capturing devices 11A and 11B captures ophthalmic images which are images of a tissue of a subject eye. The mathematical model building device 1 builds a mathematical model by training the mathematical model using a machine learning algorithm.

In a first embodiment described later, the built mathematical model outputs, based on the input ophthalmic image, a probability distribution, in which a coordinate is a random variable and in which a specific boundary/specific part exists in a region in the ophthalmic image. The ophthalmic image processing device 21 acquires the probability distribution by using a mathematical model and detects the specific boundary/specific part based on the probability distribution.

In a second embodiment described later, the built mathematical model outputs a probability distribution for identifying the tissue in the ophthalmic image based on the input ophthalmic image. The ophthalmic image processing device 21 acquires the probability distribution by using the mathematical model and acquires the degree of divergence between the acquired probability distribution and the probability distribution acquired in the case where the tissue is accurately identified as structural information indicating the degree of abnormality in the structure of the tissue.

As an example, a personal computer (hereinafter it is referred to as "PC") is used for the mathematical model building device 1 of the present embodiment. However, the device that can function as the mathematical model building device 1 is not limited to the PC. For example, the ophthalmic image capturing device 11A may function as the mathematical model building device 1. Further, controllers of a plurality of devices (for example, a CPU of the PC and a CPU 13A of the ophthalmic image capturing device 11A) may collaborate to build a mathematical model.

Details will be described later, but as an example, a mathematical model building device 1 may build the mathematical model by training the mathematical model using the ophthalmic image (hereinafter it is referred to as "training ophthalmic image") acquired from the ophthalmic image capturing device 11A and training data indicating a specific boundary/specific part of a tissue in the training ophthalmic image. Further, as another example, the mathematical model building device 1 may build the mathematical model by training the mathematical model by using the training ophthalmic image and training data indicating the position of at least one tissue in the training ophthalmic image.

Further, a PC is used for the ophthalmic image processing device 21 of the present embodiment. However, the device that can function as the ophthalmic image processing device 21 is not limited to the PC. For example, the ophthalmic image capturing device 11B, a server, or the like may function as the ophthalmic image processing device 21. Further, a mobile terminal such as a tablet terminal or a smartphone may function as the ophthalmic image processing device 21. Controllers of a plurality of devices (for example, a CPU of the PC and a CPU 13B of the ophthalmic image capturing device 11B) may collaborate to perform various processing.

When the ophthalmic image capturing device (the OCT device in the present embodiment) 11B functions as the ophthalmic image processing device 21, as an example, the ophthalmic image capturing device 11B may appropriately detect the specific boundary/specific part in the tissue of the captured ophthalmic image while capturing the ophthalmic image. When the ophthalmic image capturing device (the OCT device in the present embodiment) 11B functions as the ophthalmic image processing device 21, as another example, the ophthalmic image capturing device 11B may acquire the degree of divergence from the captured ophthalmic image while capturing the ophthalmic image.

Further, in the present embodiment, a case where a CPU is used as an example of a controller that performs various processing will be illustrated. However, it goes without saying that a controller other than the CPU may be used for at least a part of various devices. For example, by adopting a GPU as a controller, the processing speed may be increased.

The mathematical model building device 1 will be described. The mathematical model building device 1 is disposed, for example, in the ophthalmic image processing device 21 or a manufacturer that provides an ophthalmic image processing program to a user. The mathematical model building device 1 includes a control unit 2 that performs various control processing and a communication I/F 5. The control unit 2 includes a CPU 3 which is a controller that handles controls, and a storage device 4 capable of storing a program, data, and the like. The storage device 4 stores a mathematical model building program for executing mathematical model building processing (see FIG. 2) described later. Further, the communication I/F 5 connects the mathematical model building device 1 to other devices (for example, the ophthalmic image capturing device 11A and the ophthalmic image processing device 21).

The mathematical model building device 1 is connected to an operation unit 7 and a display device 8. The operation unit 7 is operated by the user in order for the user to input various instructions to the mathematical model building device 1. For the operation unit 7, for example, at least one of a keyboard, a mouse, a touch panel, and the like can be used. Note that a microphone or the like for inputting various instructions may be used together with the operation unit 7 or instead of the operation unit 7. The display device 8 displays various images. As the display device 8, various devices capable of displaying an image (for example, at least one of a monitor, a display, a projector, or the like) can be used. Note that the "image" in the present disclosure includes both a still image and a moving image.

The mathematical model building device 1 can acquire ophthalmic image data (hereinafter, it may be simply referred to as an "ophthalmic image") from the ophthalmic image capturing device 11A. The mathematical model building device 1 may acquire the ophthalmic image data from the ophthalmic image capturing device 11A by, for example, at least one of wired communication, wireless communication, an attachable and detachable storage medium (for example, a USB memory), and the like.

The ophthalmic image processing device 21 will be described. The ophthalmic image processing device 21 is disposed, for example, in a facility (for example, a hospital, a health examination facility, or the like) that performs diagnosis, examination, or the like of a person to be examined. The ophthalmic image processing device 21 includes a control unit 22 that performs various control processing and a communication I/F 25. The control unit 22 includes a CPU 23 which is a controller that handles controls, and a storage device 24 capable of storing a program, data, and the like. The storage device 24 stores an ophthalmic image processing program for executing ophthalmic image processing (for example, for the first embodiment, it is the boundary detection processing illustrated in FIG. 5, the specific part detection processing illustrated in FIG. 10, or the like, and for the second embodiment, see FIG. 13) described later. The ophthalmic image processing program includes a program that realizes a mathematical model built by the mathematical model building device 1. The communication I/F 25 connects the ophthalmic image processing device 21 to other devices (for example, the ophthalmic image capturing device 11B and the mathematical model building device 1).

The ophthalmic image processing device 21 is connected to the operation unit 27 and the display device 28. Various devices can be used for the operation unit 27 and the display device 28 in the same manner as the operation unit 7 and the display device 8 described above.

The ophthalmic image processing device 21 can acquire the ophthalmic image from the ophthalmic image capturing device 11B. The ophthalmic image processing device 21 may acquire the ophthalmic image from the ophthalmic image capturing device 11B by, for example, at least one of wired communication, wireless communication, an attachable and detachable storage medium (for example, a USB memory), and the like. Further, the ophthalmic image processing device 21 may acquire a program or the like for realizing the mathematical model built by the mathematical model building device 1 via communication or the like.

The ophthalmic image capturing devices 11A and 11B will be described. As an example, in the present embodiment, a case where the ophthalmic image capturing device 11A for providing the ophthalmic image to the mathematical model building device 1 and the ophthalmic image capturing device 11B for providing the ophthalmic image to the ophthalmic image processing device 21 are used, will be described. However, the number of ophthalmic image capturing devices used is not limited to two. For example, the mathematical model building device 1 and the ophthalmic image processing device 21 may acquire ophthalmic images from a plurality of ophthalmic image capturing devices. Further, the mathematical model building device 1 and the ophthalmic image processing device 21 may acquire the ophthalmic image from one common ophthalmic image capturing device. Note that the two ophthalmic image capturing devices 11A and 11B illustrated in the present embodiment have the same configuration. Therefore, the two ophthalmic image capturing devices 11A and 11B will be collectively described below.

Further, in the present embodiment, the OCT device is exemplified as the ophthalmic image capturing device 11 (11A, 11B). However, an ophthalmic image capturing device other than the OCT device (for example, a scanning laser ophthalmoscopy (SLO), a fundus camera, a shine-proof camera, a corneal endothelial cell image capturing device (CEM), or the like) may be used.

The ophthalmic image capturing device 11 (11A, 11B) includes a control unit 12 (12A, 12B) that performs various control processing, and an ophthalmic image capturing unit 16 (16A, 16B). The control unit 12 includes a CPU 13 (13A, 13B) which is a controller that handles controls, and a storage device 14 (14A, 14B) capable of storing a program, data, and the like.

The ophthalmic image capturing unit 16 includes various configurations necessary for capturing an ophthalmic image of a subject eye. The ophthalmic image capturing unit 16 of the present embodiment is provided with an OCT light source, a branched optical element that branches OCT light emitted from the OCT light source into measurement light and reference light, a scanning unit for scanning the measurement light, an optical system for irradiating a subject eye with the measurement light, a light receiving element for receiving combined light of the light reflected by the tissue of the subject eye and the reference light, and the like.

The ophthalmic image capturing device 11 can capture a two-dimensional tomographic image and a three-dimensional tomographic image of the fundus of the subject eye. Specifically, the CPU 13 captures the two-dimensional tomographic image of a cross section intersecting a scan line by scanning the OCT light (measurement light) on the scan line. The two-dimensional tomographic image may be an average added image generated by performing the adding and averaging processing with respect to the plurality of tomographic images of the same part. Further, the CPU 13 can capture a three-dimensional tomographic image of the tissue by scanning the OCT light two-dimensionally. For example, the CPU 13 acquires a plurality of two-dimensional tomographic images by scanning each of a plurality of scan lines having different positions with the measurement light in a two-dimensional region at a sight of the tissue from the front. Next, the CPU 13 acquires the three-dimensional tomographic image by combining the plurality of captured two-dimensional tomographic images.

(Mathematical Model Building Processing)

Figure 3:
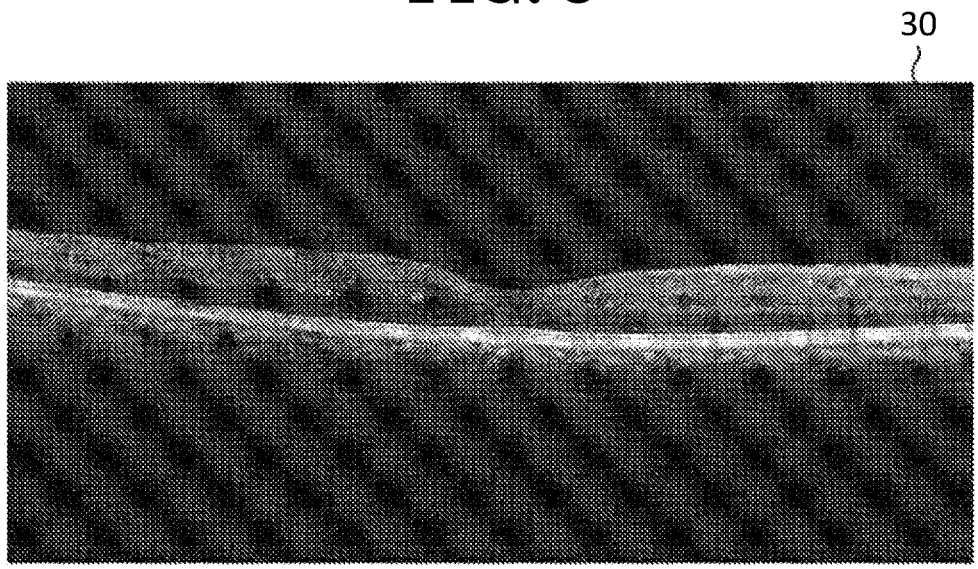
FIG. 3 is a diagram illustrating an example of a training ophthalmic image 30.
Figure 4:
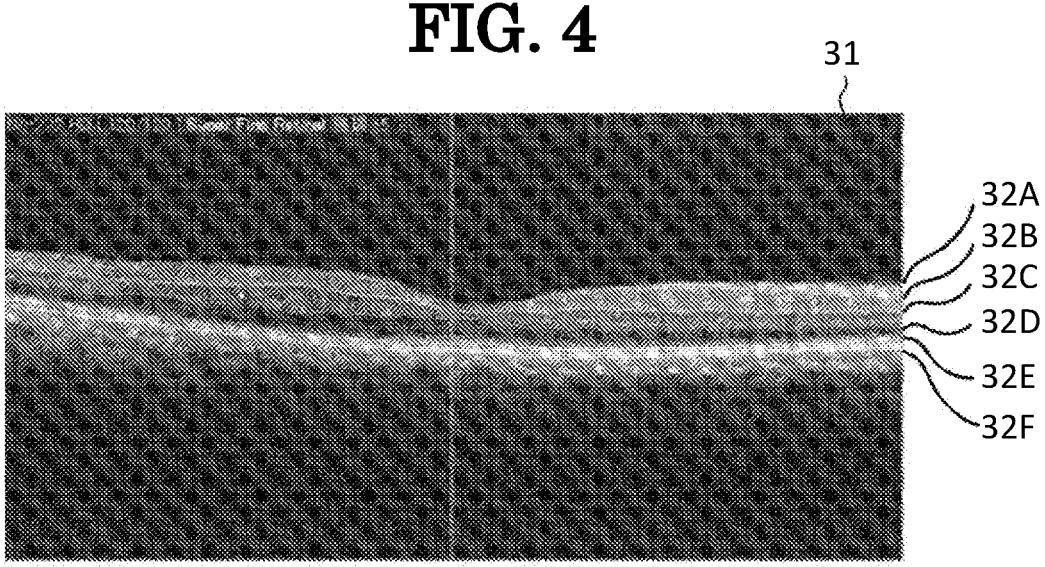
FIG. 4 is a diagram illustrating an example of training data 31.

The mathematical model building processing that is executed by the mathematical model building device 1 will be described with reference to FIGS. 2 to 4. The mathematical model building processing is executed by the CPU 3 according to the mathematical model building program stored in the storage device 4. In the mathematical model building processing, the mathematical model that outputs the probability distribution related to the tissue in the ophthalmic image is built by training the mathematical model by using the training data set. More specifically, in the first embodiment, in the mathematical model building processing, the mathematical model is built that outputs the probability distribution, in which a coordinate is a random variable and in which at least one of the specific boundary and the specific part of the tissue exists in the region in the ophthalmic image. In the second embodiment, in the mathematical model building processing, the mathematical model that outputs the probability distribution for identifying the tissue in the ophthalmic image is built. The training data set includes input side data (input training data) and output side data (output training data).

Figure 2:
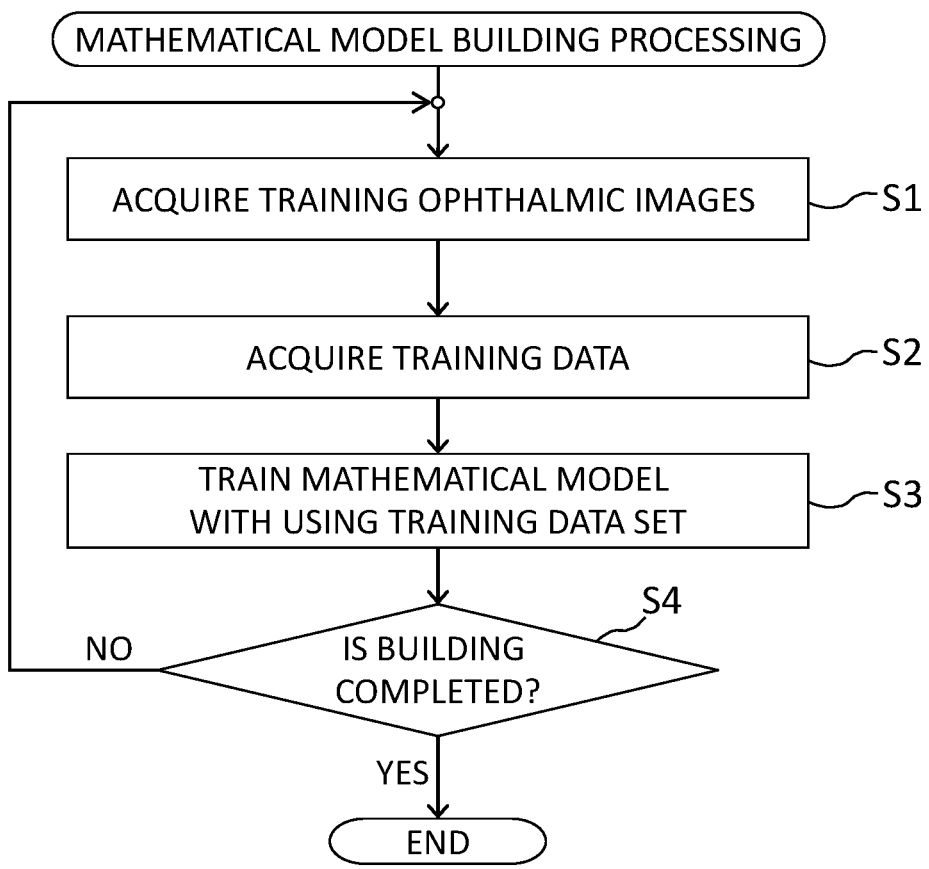
FIG. 2 is a flowchart of mathematical model building processing executed by the mathematical model building device 1.

As illustrated in FIG. 2, the CPU 3 acquires the data of the training ophthalmic image, which is the ophthalmic image captured by the ophthalmic image capturing device 11A, as the input training data (S1). In the present embodiment, the data of the training ophthalmic image is generated by the ophthalmic image capturing device 11A and then acquired by the mathematical model building device 1. However, the CPU 3 may acquire a signal (for example, an OCT signal) that is a basis for generating the training ophthalmic image from the ophthalmic image capturing device 11A and acquire the data of the training ophthalmic image data by generating the training ophthalmic image based on the acquired signal. FIG. 3 illustrates an example of the training ophthalmic image 30 which is the two-dimensional tomographic image of the fundus. The training ophthalmic image 30 illustrated in FIG. 3 represents a plurality of layers in the fundus.

Note that in the first embodiment, when the boundary detection processing (see FIG. 5) described later is executed by the ophthalmic image processing device 21, a two-dimensional tomographic image of the tissue of the subject eye (for example, the fundus) is acquired as the training ophthalmic image in S1.

Further, in the first embodiment, when the specific part detection processing (see FIG. 10) described later is executed by the ophthalmic image processing device 21, a two-dimensional front image (for example, an Enface image or the like captured by the ophthalmic image capturing device 11A, which is the OCT device) of the tissue of the subject eye (for example, the fundus) is acquired as a training ophthalmic image in S1.

However, in the first embodiment, it is also possible to change the ophthalmic image used as the training ophthalmic image. For example, when the two-dimensional front image is used as the training ophthalmic image, the training ophthalmic image may be a two-dimensional front image captured by a device other than the OCT device (for example, the SLO device or the fundus camera). The two-dimensional image other than the front image (for example, the two-dimensional tomographic image) may be used as the training ophthalmic image. Further, when the specific part is detected three-dimensionally in the specific part detection processing (see FIG. 10) described later, the three-dimensional tomographic image may be acquired as the training ophthalmic image in S1.

Further, in S1 of the second embodiment, the two-dimensional tomographic image captured by the ophthalmic image capturing device 11A, which is an OCT device, is acquired as the training ophthalmic image. Further, in the second embodiment, the ophthalmic image of the tissue having a low degree of abnormality in the structure is acquired as the training ophthalmic image. In this case, it is difficult for the mathematical model that is trained with using the training data set to identify the tissue which has a high degree of abnormality in the structure. As a result, the degree of divergence acquired for the ophthalmic image having a high degree of abnormality in the structure tends to be large.

However, in the second embodiment, it is also possible to change the ophthalmic image used as the training ophthalmic image. For example, the two-dimensional front image of the tissue of the subject eye may be used as the training ophthalmic image. In this case, various devices (for example, at least one of an OCT device, an SLO device, a fundus camera, an infrared camera, a corneal endothelial cell imaging device, or the like) can be used as the ophthalmic image capturing device for capturing the training ophthalmic image. Further, the three-dimensional image may be used as the training ophthalmic image.

Next, the CPU 3 acquires training data (S2). In the first embodiment, the training data indicates a position of at least one of the specific boundary and the specific part of the tissue in the training ophthalmic image. In the second embodiment, of the tissues in the training ophthalmic image, a position of at least one of the tissues is indicated. FIG. 4 illustrates an example of the training data 31 when the two-dimensional tomographic image of the fundus is used as the training ophthalmic image 30. The training data 31 may indicate a position of the specific boundary as an example. The training data 31 illustrated in FIG. 4 includes data of labels 32A to 32F indicating the positions of each of the six boundaries in the training ophthalmic image 30. As an example, of the plurality of tissues shown in the training ophthalmic image 30 (specifically, a plurality of layers and boundaries), data of the labels 32A to 32F indicating the positions of each of the six boundaries are included in the training data 31 illustrated in FIG. 4. In the present embodiment, the data of the labels 32A to 32F in the training data 31 is generated by a worker operating the operation unit 7 while looking at the boundary in the training ophthalmic image 30. However, it is also possible to change the method of generating data of labels.

Note that in the first embodiment, when the specific part detection processing (see FIG. 10) described later is executed by the ophthalmic image processing device 21, data indicating the position of the specific part in the tissue of the two-dimensional tomographic image or the three-dimensional tomographic image, which is the training ophthalmic image, is acquired in S2. For example, the position of the fovea is detected in the specific part detection processing described later. In this case, in S2, data indicating the position of the fovea in the two-dimensional tomographic image or the three-dimensional tomographic image is acquired.

Further, in the second embodiment, it is also possible to change the training data. For example, when the two-dimensional tomographic image of the fundus is used as the training ophthalmic image 30, the training data may be data indicating the position of at least one layer in the fundus. Further, the training data may be data indicating the position of a spot-shaped part and the like in the tissue instead of the layer and boundary.

Next, the CPU 3 uses the training data set and executes training of the mathematical model by using a machine learning algorithm (S3). As the machine learning algorithm, for example, a neural network, a random forest, a boosting, a support vector machine (SVM), and the like are generally known.

The neural network is a technique that mimics the behavior of biological nerve cell networks. The neural network includes, for example, a feed-forward (forward propagation) neural network, an RBF network (radial basis function), a spiking neural network, a convolutional neural network, a recursive neural network (a recurrent neural network, a feedback neural network, or the like), a stochastic neural network (a Boltzmann machine, a Basian network, or the like), or the like.

The random forest is a method of performing learning based on randomly sampled training data to generate a large number of decision trees. When using the random forest, branches of a plurality of decision trees that are trained in advance as an identifier are traced, and the average (or majority vote) of the results obtained from each decision tree is taken.

The boosting is a method of generating a strong identifier by combining a plurality of weak identifiers. A strong identifier is built by sequentially training a simple and weak identifier.

The SVM is a method of configuring two classes of pattern identifiers by using linear input elements. By using the training data, the SVM learns the parameters of the linear input element based on, for example, the criterion (hyperplane separation theorem) of obtaining the margin maximizing hyperplane that maximizes the distance from each data point.

The mathematical model refers, for example, to a data structure for predicting a relationship between the input data and the output data. The mathematical model is built by being trained with the training data set. As described above, the training data set is a set of input training data and output training data. For example, correlation data of each input and output (for example, weights) is updated by training.

In the present embodiment, a multi-layer neural network is used as a machine learning algorithm. The neural network includes an input layer for inputting data, an output layer for generating data to be predicted, and one or more hidden layers between the input layer and the output layer. A plurality of nodes (also called units) are disposed in each layer. Specifically, in the present embodiment, a convolutional neural network (CNN), which is a kind of multi-layer neural network, is used.

Further, the mathematical model built in the first embodiment outputs the probability distribution, in which the coordinate (either one of the one of one-dimensional coordinate, the two-dimensional coordinates, and the three-dimensional coordinates) is the random variable and in which at least one of the specific boundary and the specific part of the tissue exists inside the region in the ophthalmic image (either one of the one-dimensional region, the two-dimensional region, or the three-dimensional region). In the first embodiment, a softmax function is applied in order to have the mathematical model output the probability distribution.

In the first embodiment, when the boundary detection processing (see FIG. 5) described later is executed by the ophthalmic image processing device 21, the mathematical model built in S3 outputs the probability distribution of the coordinate where the specific boundary exists, in the one-dimensional region on a line extending in a direction (in the present embodiment, the A-scan direction of OCT) intersecting the specific boundary in the two-dimensional tomographic image.

Further, in the first embodiment, when the specific part detection processing (see FIG. 10) described later is executed by the ophthalmic image processing device 21, the mathematical model built in S3 outputs the probability distribution, in which the two-dimensional coordinates are the random variables and in which the specific part (for example, the fovea in the present embodiment) exists in the two-dimensional region in the two-dimensional ophthalmic image.

As an example, the mathematical model built in the second embodiment outputs the probability distribution, in which the coordinate (either one of the one-dimensional coordinate, two-dimensional coordinates, three-dimensional coordinates, and four-dimensional coordinates) is the random variable and in which the specific tissue (for example, a specific boundary, a specific layer, a specific part, or the like) exists inside the region (either one of the one-dimensional region, two-dimensional region, three-dimensional region, and four-dimensional region that includes the time axis) in the ophthalmic image, as a probability distribution for identifying the tissue. In the second embodiment, a softmax function is applied in order to have the mathematical model output the probability distribution. Specifically, the mathematical model built in S3 outputs the probability distribution, in which the coordinate is a random variable and in which the specific boundary exists in the one-dimensional region extending in the direction (in the present embodiment, it is the A-scan direction of OCT) intersecting the specific boundary in the two-dimensional tomographic image.

However, in the second embodiment, the specific method for outputting the probability distribution for the mathematical model to identify the tissue can be changed as appropriate. For example, the mathematical model may output the probability distribution, in which the two-dimensional coordinates or three-dimensional coordinates are random variables and in which the specific tissue (for example, the characteristic part) exists in the two-dimensional region or the three-dimensional region, as a probability distribution for identifying the tissue. Further, the mathematical model may output the probability distribution in which the type of a plurality of tissues (for example, a plurality of layers and boundaries) in the subject eye is a random variable, for each region (for example, for each pixel) of the input ophthalmic image. Further, the ophthalmic image input into the mathematical model may be a moving image.

Further, other machine learning algorithms may be used. For example, a hostile generative network (Generative adversarial networks: GAN) that utilizes two competing neural networks may be adopted as a machine learning algorithm.

The processes S1 to S3 are repeated until the building of the mathematical model is completed (S4: NO). When the building of the mathematical model is completed (S4: YES), the mathematical model building processing ends. The program and data for realizing the built mathematical model are incorporated in the ophthalmic image processing device 21.

(Ophthalmic Image Processing)

Ophthalmic image processing executed by the ophthalmic image processing device 21 will be described with reference to FIGS. 5 to 17. The ophthalmic image processing is executed by the CPU 23 according to the ophthalmic image processing program stored in the storage device 21.

(Boundary Detection Processing)

Boundary detection processing, which is an example of the ophthalmic image processing according to the first embodiment, will be described with reference to FIGS. 5 to 9. In the boundary detection processing, the specific boundary (in the first embodiment, the two-dimensional boundary, and the three-dimensional boundary) is detected based on the probability distribution, in which the one-dimensional coordinate is the random variable and in which the specific boundary exists in each of a plurality of one-dimensional regions. Further, an Enface image of a specific layer in the tissue is acquired based on the detected three-dimensional boundary.

First, the CPU 23 acquires the three-dimensional tomographic image of the tissue of the subject eye (the fundus in the first embodiment) (S11). The three-dimensional tomographic image is captured by the ophthalmic image capturing device 11B and acquired by the ophthalmic image processing device 21. As described above, the three-dimensional tomographic image is composed by combining a plurality of two-dimensional tomographic images captured by scanning on different scan lines with the measurement light. Note that the CPU 23 may acquire a signal (for example, an OCT signal) that is a basis for generating a three-dimensional tomographic image from the ophthalmic image capturing device 11B and generate the three-dimensional tomographic image based on the acquired signal.

Figure 6:
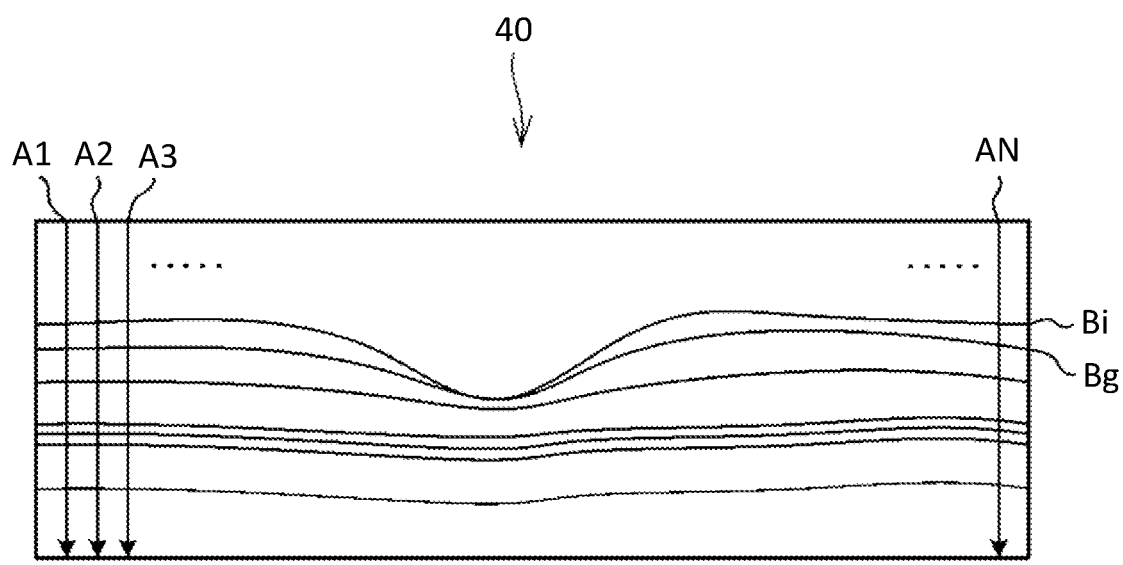
FIG. 6 is a diagram schematically illustrating a relationship between a two-dimensional tomographic image 40 input into a mathematical model and one-dimensional regions A1 to AN in the two-dimensional tomographic image 40.

The CPU 23 extracts the T-th (an initial value of T is "1") two-dimensional tomographic image from the plurality of two-dimensional tomographic images constituting the acquired three-dimensional tomographic image (S12). FIG. 6 illustrates an example of the two-dimensional tomographic image 40. The two-dimensional tomographic image 40 represents a plurality of boundaries in the fundus of the subject eye. In the example illustrated in FIG. 6, a plurality of boundaries including a boundary Bi, which is an inner limiting membrane (ILM), and a boundary Bg between a nerve fiber layer (NFL) and a ganglion cell layer (GCL)

appear. Further, a plurality of one-dimensional regions A1 to AN are set in the two-dimensional tomographic image 40. In the first embodiment, the plurality of one-dimensional regions A1 to AN set in the two-dimensional tomographic image 40 extend along an axis that intersects the specific boundary (in the first embodiment, the plurality of boundaries including the boundary Bi and boundary Bg). Specifically, the one-dimensional regions A1 to AN of the first embodiment match each region of a plurality (N) of A-scans constituting the two-dimensional tomographic image 40 captured by the OCT device.

Note that it is also possible to change the method of setting the plurality of one-dimensional regions. For example, the CPU 23 may set the plurality of one-dimensional regions so that the angle between the axis of each one-dimensional region and the specific boundary is as close to vertical as possible. In this case, the position and angle of each one-dimensional region may be set so that the angle approaches vertically, for example, based on the shape of a general tissue of the subject eye (the fundus in the first embodiment).

Figure 7:
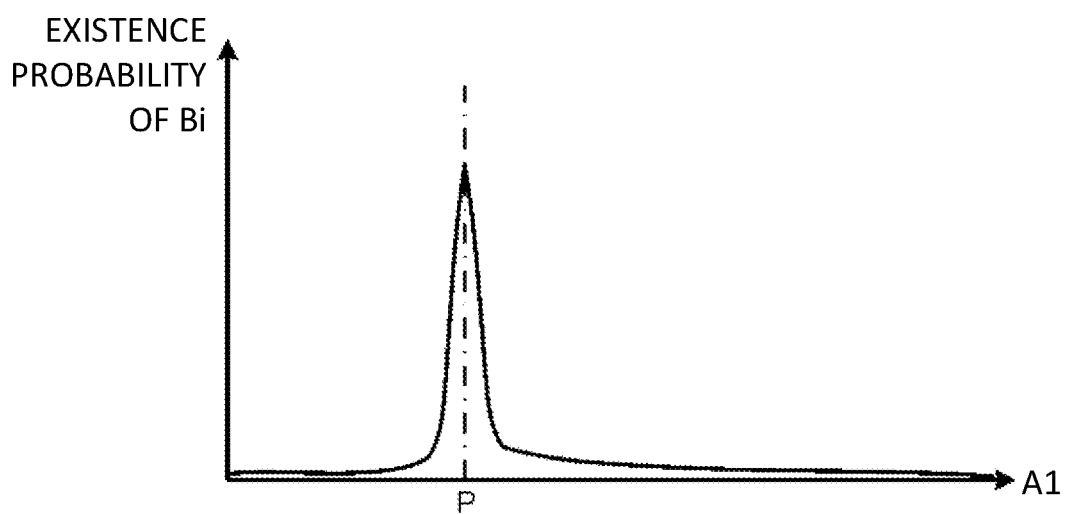
FIG. 7 is an example of a graph illustrating a probability distribution of a coordinate where a boundary Bi exists, in which a one-dimensional coordinate of the one-dimensional region A1 is a random variable.

By inputting the T-th two-dimensional tomographic image into the mathematical model, the CPU 23 acquires the probability distribution of the coordinate where the M-th boundary (an initial value of M is "1") exists in each of the plurality of one-dimensional regions A1 to AN (S14). FIG. 7 illustrates an example of a graph showing the probability distribution of the coordinate where the boundary Bi exists, which is acquired from the one-dimensional region A1. In the example illustrated in FIG. 7, the probability distribution of the coordinate where the boundary Bi exists is illustrated, in which the one-dimensional coordinate of the one-dimensional region A1 is a random variable. That is, in the example illustrated in FIG. 7, the horizontal axis is a random variable, the vertical axis is the probability of the random variable, and the random variable is the coordinate where the boundary Bi exists in the one-dimensional region A1. In S14, the probability distributions in each of the plurality of one-dimensional regions A1 to AN are acquired.

According to the graph illustrated in FIG. 7, among each of the points on the one-dimensional region A1, the point at which the boundary Bi is most likely to exist can be determined to be the point P. Further, even when the structure of the tissue is collapsed due to the influence of the disease, or when the image quality of at least a part of the ophthalmic image is not good, or the like, the probability distribution output by the mathematical model has a high possibility of forming a peak at any position. Therefore, by using the probability distribution output in S14, the boundary is detected appropriately and directly.

The CPU 23 acquires a probability map that two-dimensionally shows the ratio of the existence of the M-th boundary with respect to the M-th boundary in the T-th two-dimensional tomographic image. The CPU 23 displays the acquired probability map on the display device 28 (S15). The probability map is generated by arranging a plurality of probability distributions acquired for each of the plurality of one-dimensional regions A1 to AN in two dimensions. The probability map may be generated by the CPU 23 based on the plurality of probability distributions. Further, the probability map may be generated by the mathematical model.

Figure 8:
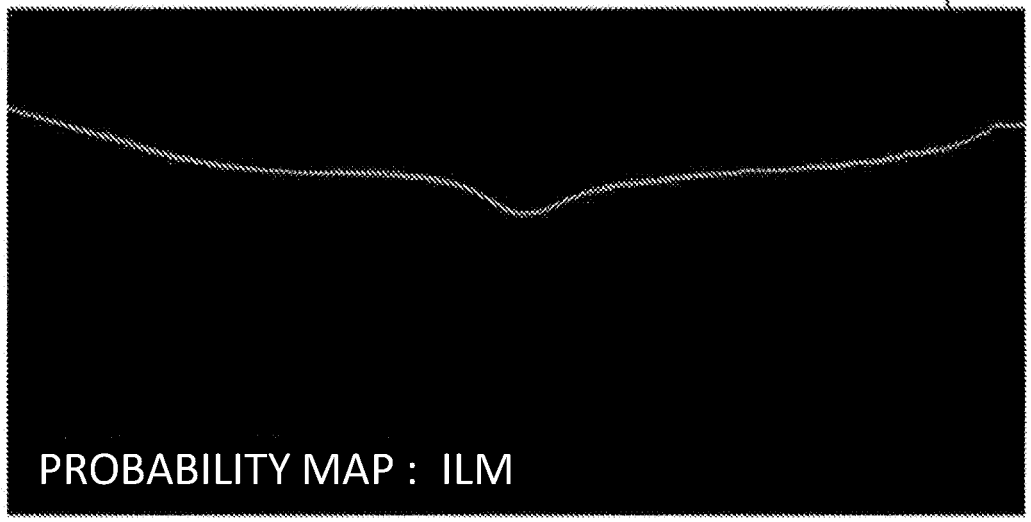
FIG. 8 is a diagram illustrating an example of a probability map of the boundary Bi, which is an inner limiting membrane (ILM).
Figure 9:
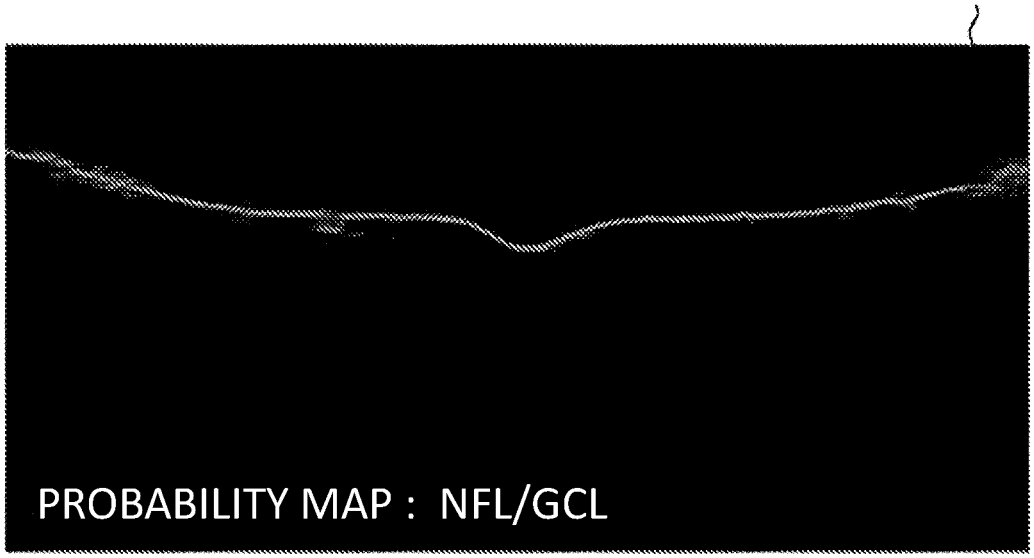
FIG. 9 is a diagram illustrating an example of a probability map of a boundary Bg between a nerve fiber layer (NFL) and a ganglion cell layer (GCL).

FIG. 8 illustrates an example of the probability map 41 of the boundary Bi, which is an inner limiting membrane (ILM). FIG. 9 illustrates an example of the probability map 42 of the boundary Bg between the nerve fiber layer (NFL) and the ganglion cell layer (GCL). In the probability maps 41 and 42 illustrated in FIGS. 8 and 9, the values for each coordinate are expressed by luminance, and the position that seems to be a specific boundary becomes brighter. Therefore, the user can appropriately recognize the positions of the boundaries Bi and Bg two-dimensionally by looking at the displayed probability maps 41 and 42. Note that needless to say, the expression method of the probability map can be changed as appropriate.

Next, the CPU 23 detects the M-th boundary of the two-dimensional tomographic image based on the probability distribution related to the M-th boundary acquired for each of the plurality of one-dimensional regions A1 to AN (S16). In the first embodiment, the CPU 23 detects the two-dimensional boundary by combining the plurality of probability distributions acquired for each of the plurality of one-dimensional regions A1 to AN. The two-dimensional boundary may be detected based on the plurality of probability distributions acquired in S14 or may be detected based on the probability map acquired in S15. Further, the mathematical model may output the boundary detection result, or the CPU 23 may perform the boundary detection processing.

Note that in the first embodiment, the post-processing is performed with respect to the probability distributions related to the plurality of one-dimensional regions A1 to AN, and then the probability map generation and the boundary detection are performed. As an example, a boundary on the n-th one-dimensional region may be detected based on the probability distribution on the n-th one-dimensional region and the probability distribution on the one-dimensional region positioned in the vicinity of the n-th one-dimensional region. In this case, for example, a known method such as graph cut may be adopted. Further, the boundary may be detected by using the theory of the shortest path search for finding the path having the minimum weight.

Further, the CPU 23 may superimpose and display the probability maps 41 and 42 or the detected specific boundaries on the two-dimensional tomographic image (that is, raw image) that is a target for detecting the boundary. In this case, a positional relationship between an actually captured tissue and the boundary detected by using the probability distribution is appropriately recognized. Further, the CPU 23 may input the instruction for designating the position of the boundary in the tissue from the user in a state where the probability maps 41 and 42 or the detected boundary are superimposed and displayed on the raw image. In this case, the user can appropriately designate the position of the boundary while comparing the boundary that is detected by using the probability distribution with the image of the tissue actually captured.

Next, the CPU 23 determines whether or not the detection of all the boundaries to be detected in the T-th two-dimensional tomographic image is completed (S18). When the detection of a part of the boundaries is not completed (S18: NO), "1" is added to the boundary order M (S19), the process returns to S14, and the next boundary detection processing is executed (S14 to S16). When the detection of all the boundaries is completed (S18: YES), the CPU 23 determines whether or not the detection of the boundaries of all the two-dimensional tomographic images constituting the three-dimensional tomographic image is completed (S21). When the detection of the boundary of a part of the two-dimensional tomographic images is not completed (S21: NO), "1" is added to the order T of the two-dimensional tomographic images (S22), the process returns to S12, and the boundary of the next two-dimensional tomographic image is detected (S12 to S19).

When the detection of the boundaries of all the two-dimensional tomographic images is completed (S21: YES), the detection of the three-dimensional boundaries is completed. The CPU 23 acquires the three-dimensional boundary by integrating the plurality of two-dimensional boundaries detected in S16 with respect to at least one of the M boundaries (S24). Note that the CPU 23 can generate data of the detected three-dimensional boundary image and display the generated data on the display device 28. Therefore, the user can appropriately recognize the three-dimensional shape of the boundary. Further, the probability map showing the probability distribution in the three-dimensional region may be generated based on the acquisition result of the probability distribution with respect to T two-dimensional tomographic images.

Next, the CPU 23 acquires an Enface image of the specific layer (which may be a boundary) included in the three-dimensional tomographic image based on the detected three-dimensional boundary and the three-dimensional tomographic image acquired in S11 (S25). The Enface image is a two-dimensional front image when the specific layer is viewed from a direction along the optical axis of the measurement light of OCT. The Enface image acquired in S25 has high quality because the image is generated based on the detected boundary that is appropriately detected. Note that in S25, an Enface image with respect to a specific one of the plurality of layers and boundaries included in the three-dimensional image may be acquired. Further, an Enface image with respect to a plurality of layers and boundaries among the plurality of layers and boundaries included in the three-dimensional image may be acquired.

Further, the CPU 23 may acquire a thickness map showing the distribution of the thickness of a specific layer included in the three-dimensional tomographic image in two dimensions based on the three-dimensional tomographic image acquired in S11 and the detected three-dimensional boundary. In this case, the specific layer is specified based on the appropriately detected boundary, and a more accurate thickness map is acquired.

Figure 5:
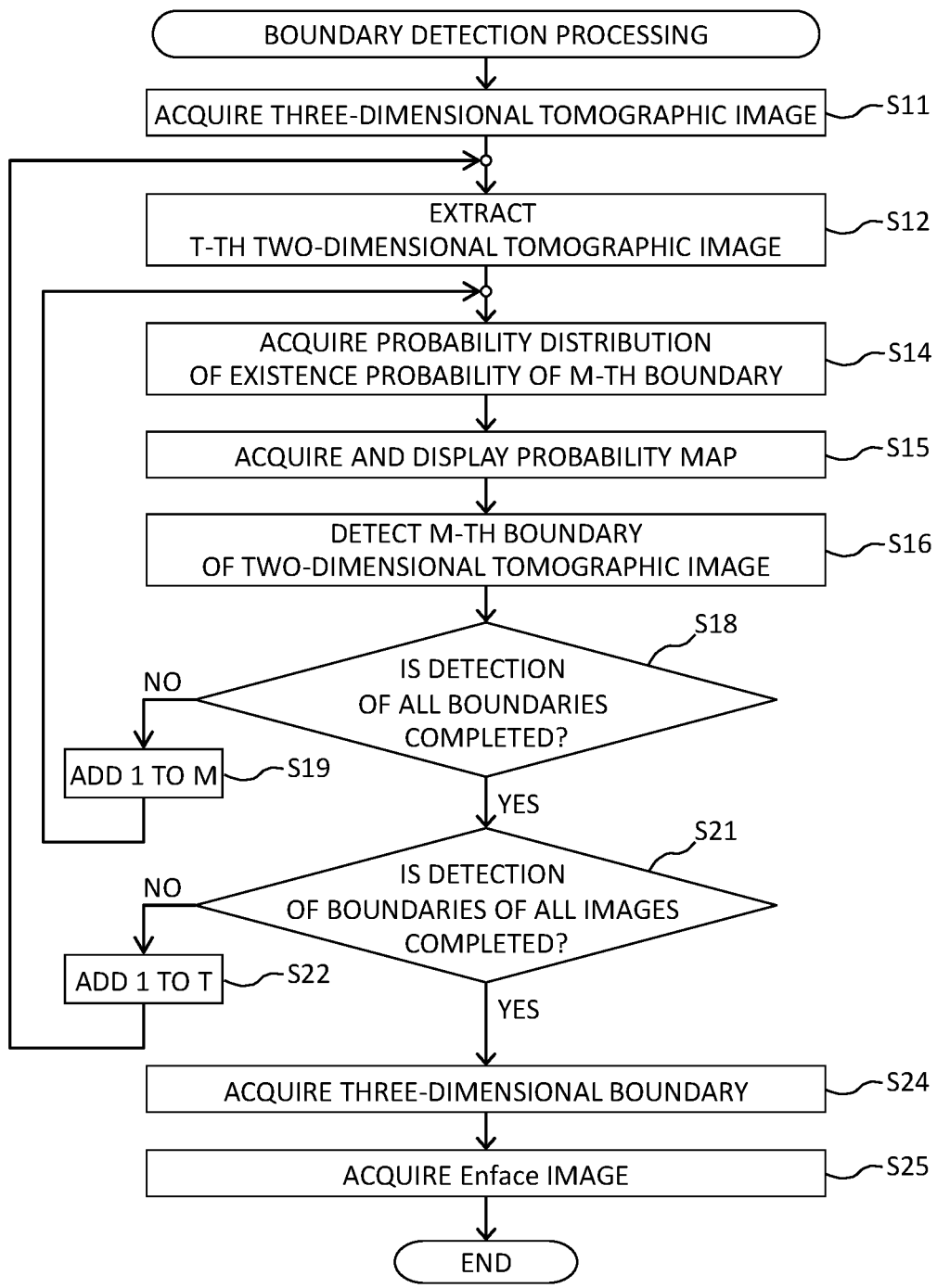
FIG. 5 is a flowchart of boundary detection processing executed by the ophthalmic image processing device 21.

Note that in the example illustrated in FIG. 5, after the three-dimensional tomographic image is acquired in S11, the specific boundary is detected in two dimensions and three dimensions. Further, the Enface image is acquired based on the detected three-dimensional boundary. However, only the two-dimensional boundary may be detected. In this case, the two-dimensional ophthalmic image may be acquired in S11. Further, in the example illustrated in FIG. 5, in S14, the plurality of probability distributions for each of the plurality of one-dimensional regions A1 to AN are acquired. As a result, the two-dimensional boundary is detected. However, for example, when only one point on a specific boundary needs to be detected, in S14, only the probability distribution in one region of one dimension may be acquired.

(Specific Part Detection Processing)

Specific part detection processing, which is an example of the ophthalmic image processing according to the first embodiment, will be described with reference to FIGS. 10 to 12. In the specific part detection processing, the specific part is detected based on the probability distribution of the coordinate where the specific part exists. In the following, a case where the specific part is detected from the two-dimensional ophthalmic image will be illustrated.

First, the CPU 23 acquires an ophthalmic image of the tissue of the subject eye (the fundus in the first embodiment) (S31). As an example, in S31 of the first embodiment, the two-dimensional front image (for example, an Enface image or a motion contrast image) captured by the OCT device is acquired. However, the ophthalmic image acquired in S31 can be changed as appropriate. For example, the two-dimensional front image captured by an SLO device, a fundus camera, or the like may be acquired in S31. Further, the ophthalmic image obtained by capturing the tissue other than the fundus may be acquired in S31.

Figure 11:
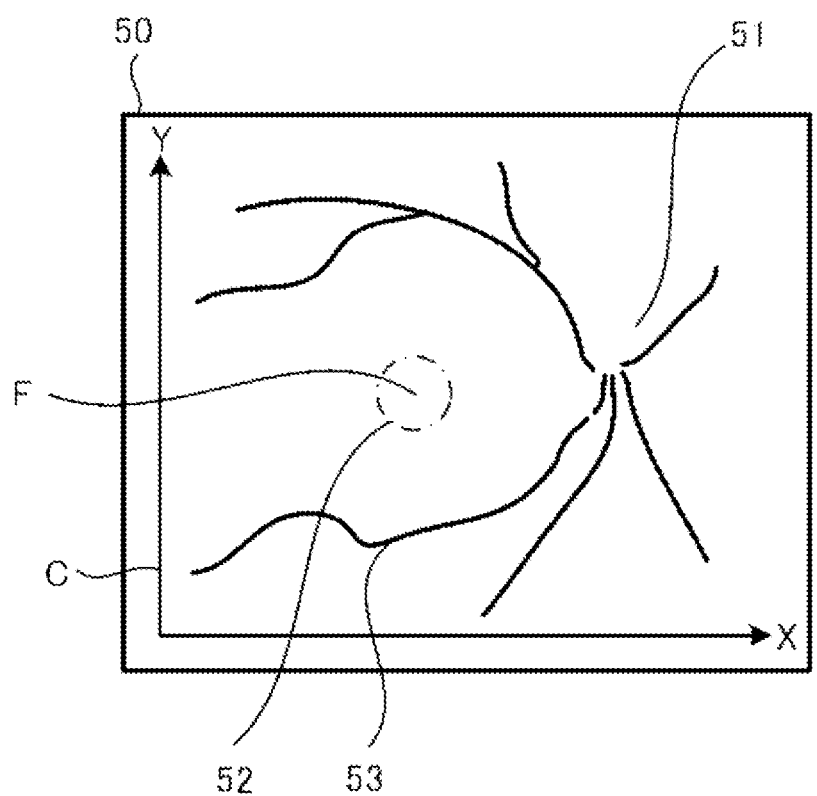
FIG. 11 is a diagram schematically illustrating a relationship between an ophthalmic image 50 input into the mathematical model and a coordinate system C of the two-dimensional coordinates in the ophthalmic image 50.

FIG. 11 illustrates an example of the ophthalmic image 50 acquired in S31 of the first embodiment. In the two-dimensional ophthalmic image 50 illustrated in FIG. 11, an optic nerve head S1, a macula 52, and a fundus blood vessel 53 in the fundus are shown. The center of the macula 52 is the fovea F. Further, a two-dimensional coordinates system (XY coordinates) is set in the two-dimensional region C in the two-dimensional ophthalmic image 50.

By inputting the ophthalmic image 50 into the mathematical model, the CPU 23 acquires the probability distribution, in which the two-dimensional coordinates are the random variables and in which the specific part exists in the two-dimensional region in the ophthalmic image 50 (S32). As an example, the specific part in the first embodiment is the fovea F. However, it goes without saying that the specific part is not limited to the fovea F. For example, the specific part may be the optic nerve head or the like. Further, the specific part may be a single point or may be a part having a certain region or volume. The CPU 23 detects the specific part in the two-dimensional ophthalmic image 50 based on the probability distribution acquired in S32 (S33).

Figure 12:
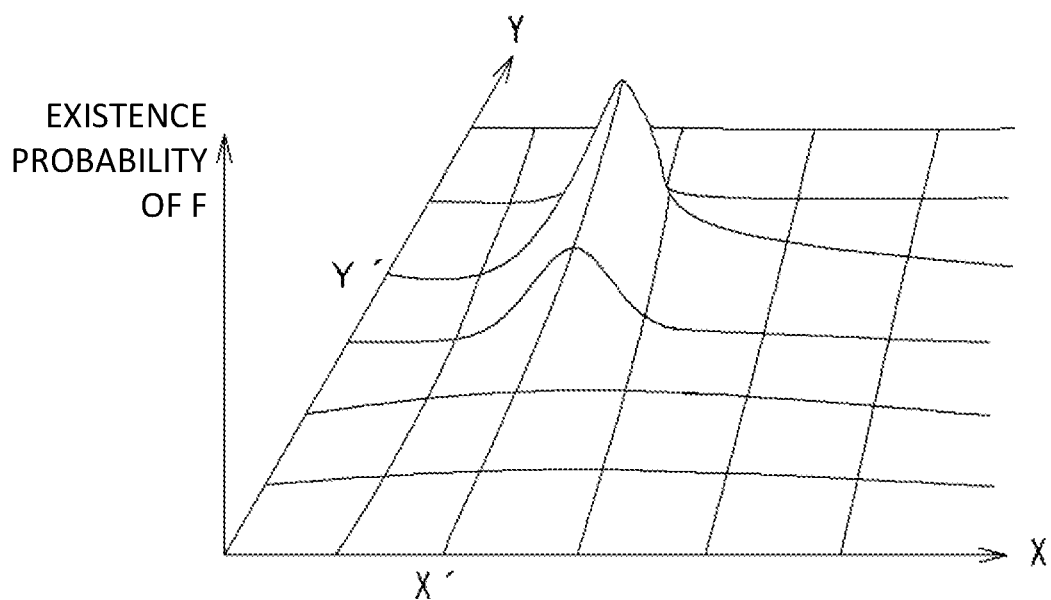
FIG. 12 is an example of a graph illustrating a probability distribution of coordinates where a specific part exists, in which the two-dimensional coordinates are random variables.

FIG. 12 illustrates an example of a graph showing the probability distribution acquired from the two-dimensional coordinates system, in which the coordinates where the specific part exists are random variables. In the example illustrated in FIG. 12, the X axis and the Y axis are random variables, the axes orthogonal to the X axis and the Y axis are the probabilities of the random variables, and the random variable is the coordinates where the fovea F exists in the two-dimensional region C. According to the graph illustrated in FIG. 12, it can be determined that among each of the points in the two-dimensional region C, the coordinates of the point where the fovea F is most likely to exist are (X', Y'). Further, even when the structure of the tissue is collapsed due to the influence of the disease, or when the image quality of at least a part of the ophthalmic image is not good, or the like, the probability distribution output by the mathematical model has a high possibility of forming a peak at any position. Therefore, the specific part is appropriately and directly detected.

Note that in the specific part detection processing, it is also possible to detect the specific part from a three-dimensional ophthalmic image. In this case, in S31, the three-dimensional ophthalmic image (for example, the three-dimensional tomographic image captured by the OCT device) is acquired. In S32, the probability distribution is acquired in which the three-dimensional coordinates are the random variables and in which the specific part exists in the three-dimensional region in the three-dimensional ophthalmic image. In S33, the specific part in the three-dimensional ophthalmic image is detected based on the probability distribution acquired in S32.

Next, the ophthalmic image processing according to the second embodiment will be described with reference to FIGS. 13 to 17. Note that the description of the same processing as the ophthalmic image processing according to the first embodiment will be omitted or simplified.

First, the CPU 23 acquires the three-dimensional tomographic image of the tissue of the subject eye (the fundus in the second embodiment) in the same manner as S11 of the boundary detection processing which is an example of the ophthalmic image processing according to the first embodiment (S31). Next, similar to S12 of the boundary detection processing, the CPU 23 extracts the T-th (an initial value of T is "1") two-dimensional tomographic image from the plurality of two-dimensional tomographic images constituting the acquired three-dimensional tomographic image (S32).

Figure 14:
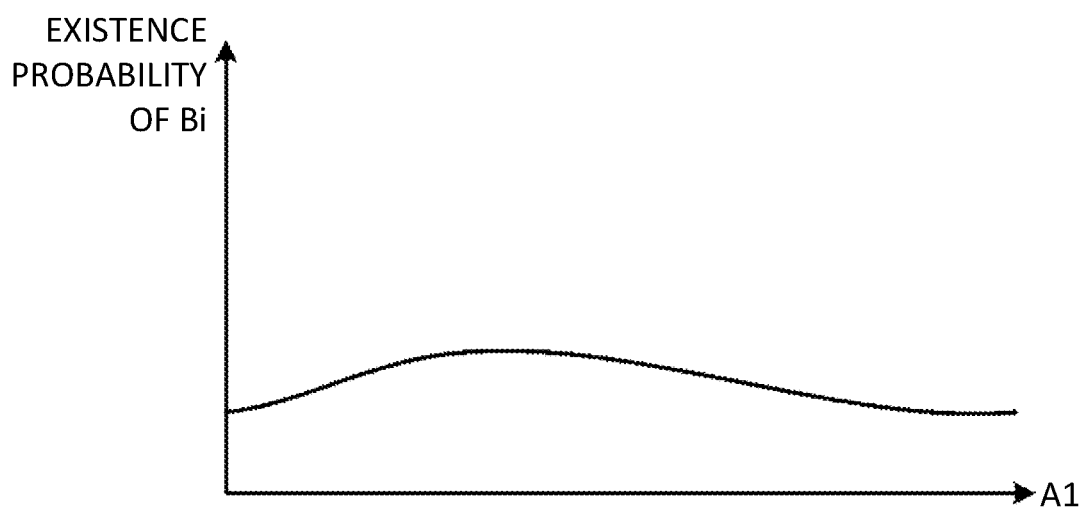
FIG. 14 is an example of a graph illustrating a probability distribution for identifying the boundary Bi in a case where the degree of abnormality in a structure in the vicinity of the boundary Bi is high.

By inputting the T-th two-dimensional tomographic image into the mathematical model, the CPU 23 acquires the probability distribution of the coordinate where the M-th boundary (an initial value of M is "1") exists in each of the plurality of one-dimensional regions A1 to AN, as a probability distribution for identifying the tissue (S34). FIGS. 7 and 14 illustrate an example of a graph showing the probability distribution of the coordinate where the boundary Bi exists, which is acquired from the one-dimensional coordinate A1. In the example illustrated in FIGS. 7 and 14, the probability distribution of the coordinate where the boundary Bi exists is illustrated, in which the one-dimensional coordinate of the one-dimensional region A1 is a random variable. That is, in the example illustrated in FIGS. 7 and 14, the horizontal axis is a random variable, the vertical axis is the probability of the random variable, and the random variable is the coordinate where the boundary Bi exists in the one-dimensional region A1. In S34, the probability distributions in each of the plurality of one-dimensional regions A1 to AN are acquired.

In the second embodiment, the probability distribution illustrated in FIG. 7 is an example of the probability distribution output in the case where the degree of abnormality in the structure of the tissue (specifically, the tissue in the vicinity of the boundary Bi) is low. At a position where the degree of abnormality in the structure is low, the tissue is easily identified accurately by using the mathematical model, so the probability of the position of the tissue tends to be biased. According to the graph illustrated in FIG. 7, among each of the points on the one-dimensional region A1, the point at which the boundary Bi is most likely to exist can be determined to be the point P. The probability distribution (that is, the ideal probability distribution) acquired in the case where the mathematical model accurately identifies the tissue takes a value of 1 at only one point on the one-dimensional region A1 and is 0 at the other points.

On the other hand, the probability distribution illustrated in FIG. 14 is an example of the probability distribution output in the case where the degree of abnormality in the structure of the tissue is high. As illustrated in FIG. 14, the probability distribution is less likely to be biased at a position where the degree of abnormality in the structure is high. As described above, the bias of the probability distribution for identifying the tissue changes according to the degree of abnormality in the structure of the tissue.

Next, the CPU 23 acquires the degree of divergence of the probability distribution P related to the M-th boundary (S35). The degree of divergence is a difference of the probability distribution P acquired in S14 with respect to the probability distribution acquired in the case where the tissue is accurately identified. In the second embodiment, the degree of divergence is acquired as the structural information indicating the degree of abnormality in the structure of the tissue. In S35 of the second embodiment, the degree of divergence is acquired (calculated) for each of the plurality of probability distributions P acquired for the plurality of one-dimensional regions A1 to AN.

In the second embodiment, the entropy of the probability distribution P is calculated as the degree of divergence. The entropy is given by the following (Equation 1). The entropy H(P) takes a value of 0≤H(P)≤log (number of events) and becomes a smaller value as the probability distribution P is biased. That is, the smaller the entropy H(P), the lower the degree of abnormality in the structure of the tissue. The entropy of the probability distribution acquired in the case where the tissue is accurately identified is 0. Further, the entropy H(P) increases as the degree of abnormality in the structure of the tissue increases and it becomes difficult to identify the tissue. Therefore, by using the entropy H(P) of the probability distribution P as the degree of divergence, the degree of abnormality in the structure of the tissue is appropriately quantified.

$$H(P) = -\Sigma p \log(p) \quad \text{(Equation 1)}$$

However, a value other than entropy may be adopted as the degree of divergence. For example, at least one of the standard deviation, the coefficient of variation, the variance, and the like indicating the degree of dispersion of the acquired probability distribution P may be used as the degree of divergence. The KL divergence or the like, which is a measure for measuring the difference between probability distributions P, may be used as the degree of divergence. Further, the maximum value of the acquired probability distribution P (for example, the maximum value of the probabilities illustrated in FIGS. 7 and 14) may be used as the degree of divergence. Further, the difference between the maximum value of the acquired probability distribution P and the second largest value may be used as the degree of divergence.

Next, the CPU 23 determines whether or not the degree of divergence of all the boundaries to be detected in the T-th two-dimensional tomographic image is acquired (S36). When the degree of divergence of a part of the boundary is not acquired (S16: NO), "1" is added to the order M of the boundary (S37), the process returns to S14, and the degree of divergence of the next boundary is acquired (S34, S35). When the degree of divergence of all the boundaries is acquired (S36: YES), the CPU 23 stores the degree of divergence of the T-th two-dimensional tomographic image in the storage device 24 and displays the degree of divergence on the display device 28 (S39). The CPU 23 acquires (generates in the second embodiment) a degree of structural abnormality graph of the T-th two-dimensional tomographic image and displays the graph on the display device 28 (S40).

The degree of structural abnormality graph 52 will be described with reference to FIGS. 15 and 16. FIG. 15 illustrates an example of a display screen on which a two-dimensional tomographic image 51A having a low degree of abnormality in the structure, a degree of structural abnormality graph 52A related to the two-dimensional tomographic image 51A, and a degree of divergence table 53A showing the degree of divergence related to the two-dimensional tomographic image 51A are displayed. Further, FIG. 16 illustrates an example of a display screen on which a two-dimensional tomographic image 51B having a high degree of abnormality in the structure, a degree of structural abnormality graph 52B related to the two-dimensional tomographic image 51B, and a degree of divergence table 53B showing the degree of divergence related to the two-dimensional tomographic image 51B are displayed.

As illustrated in FIGS. 15 and 16, the two-dimensional tomographic image S1 is a two-dimensional image spreading in the X direction (horizontal direction of the drawing) and the Z direction (vertical direction of the drawing). As described above, the degree of divergence is acquired for each of a plurality of axes extending parallel to the Z direction on the ophthalmic image (in the second embodiment, the plurality of A-scans). In the degree of structural abnormality graph 52 illustrated in FIGS. 9 and 10, the horizontal axis is the X axis, and the degree of divergence at each of the positions in the X direction is shown on the vertical axis.

As an example, in the degree of structural abnormality graph 52 of the second embodiment, the average value of the plurality of degrees of divergence (the entropy in the second embodiment) acquired for each of the plurality of boundaries is shown for each position in the X direction. However, the degree of divergence of one boundary may be shown with the degree of structural abnormality graph 52. Further, the average value of the plurality of specific boundaries (for example, the boundary of IPL/INL and the boundary of OPL/ONL) may be shown with the degree of structural abnormality graph 52. Further, instead of the average value, various statistical values other than the average value (for example, a median value, a mode value, the maximum value, the minimum value, or the like) may be used.

As illustrated in FIG. 15, when the degree of abnormality in the structure is low in the entire X direction, the degree of divergence shown with the degree of structural abnormality graph 52A becomes a low value in the entire X direction. On the other hand, as illustrated in FIG. 16, at the position in the X direction where the degree of abnormality in the structure is high, the degree of divergence shown with the degree of structural abnormality graph 52B becomes a high value. As described above, according to the degree of structural abnormality graph 52, the user can appropriately recognize which position in the X direction has a high degree of abnormality.

An example of a method of displaying the degree of divergence will be described with reference to FIGS. 15 and 16. As shown in FIGS. 15 and 16, in the degree of divergence table 53 of the present embodiment, the acquired degree of divergence (the entropy in the present embodiment) is displayed for each of the plurality of boundaries. Therefore, the user can appropriately recognize the boundary having a high degree of abnormality in the structure based on the quantified value. The degree of divergence displayed in the degree of divergence table 53 of the second embodiment is the average value of the plurality of degrees of divergence acquired for each of the plurality of one-dimensional regions (the A-scan in the present embodiment). Further, in the degree of divergence table 53 of the present embodiment, the average value of the degree of divergence related to all the boundaries is displayed. Therefore, the user can easily recognize from the average value whether or not there is a part having a high degree of abnormality in the structure in the tissue shown in the ophthalmic image. Further, in the degree of divergence table 53 of the second embodiment, the average value of the degree of divergence related to the plurality of specific boundaries of all the boundaries is displayed. As an example, in the second embodiment, the average value of the boundaries (the IPL/INL boundary and the OPL/ONL boundary) in which the structure tends to collapse due to the influence of the disease is displayed. Therefore, the user can easily recognize whether or not there is a structural abnormality due to the disease. Note that as described above, various statistical values other than the average value may be used.

Next, the CPU 23 determines whether or not the degree of divergence of all the two-dimensional tomographic images constituting the three-dimensional tomographic image is acquired (S41). When the degree of divergence of a part of the two-dimensional tomographic images is not acquired (S41: NO), "1" is added to the order T of the two-dimensional tomographic images (S42), the process returns to S12, and the degree of divergence of the next two-dimensional tomographic image is acquired (S32 to S40). When the degree of divergence of all the two-dimensional tomographic images is acquired (S41: YES), the CPU 23 acquires (generates in the second embodiment) the degree of structural abnormality map and displays the map on the display device 28 (S44).

Figure 17:
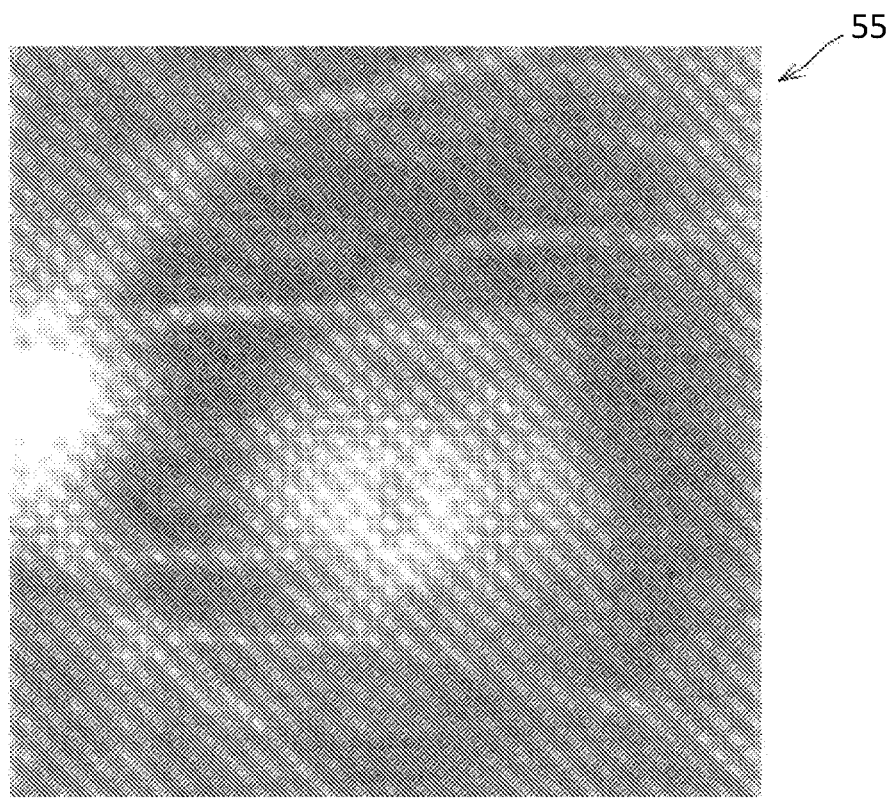
FIG. 17 is a diagram illustrating an example of a degree of structural abnormality map 55.

The degree of structural abnormality map 55 will be described with reference to FIG. 17. The degree of structural abnormality map 55 is a map showing the two-dimensional distribution of the degree of divergence in the tissue. As described above, in the second embodiment, the degree of divergence is acquired for each of the plurality of two-dimensional tomographic images constituting the three-dimensional tomographic image. That is, the degree of divergence of the entire tissue shown in the three-dimensional tomographic image is acquired. The degree of structural abnormality map 55 of the second embodiment shows the two-dimensional distribution of the degree of divergence when the tissue (the fundus in the second embodiment) is viewed from the front. However, the direction indicating the two-dimensional distribution can be changed as appropriate. Further, in the degree of structural abnormality map 55 of the second embodiment, the higher the degree of divergence, the lower the displayed luminance. However, the specific method for showing the degree of divergence of each position in the degree of structural abnormality map 55 can also be changed as appropriate. Further, in the degree of structural abnormality map 55 of the second embodiment, the average value of the degree of divergence related to the plurality of boundaries is used. However, the degree of divergence related to the specific boundary may be used.

Next, when there is a part in which the degree of divergence thereof is equal to or higher than the threshold value (hereinafter it is referred to as "abnormal part") in the tissue shown in the ophthalmic image (the three-dimensional tomographic image in the second embodiment), the CPU 23 displays a tomographic image (at least one of the two-dimensional tomographic image and the three-dimensional tomographic image) or an enlarged image of the abnormal part on the display device 28 (S45). Therefore, the user can appropriately check the image of the abnormal part.

Specifically, of the plurality of ophthalmic images (in the present embodiment, the plurality of two-dimensional tomographic images constituting the three-dimensional tomographic image) obtained by capturing the tissue of the same subject eye, the CPU 23 of the second embodiment displays the ophthalmic image having the highest degree of divergence or the ophthalmic image having the degree of divergence equal to or higher than the threshold value on the display device 28. For example, of the plurality of ophthalmic images, the CPU 23 may display the ophthalmic image having a high degree of divergence on a capture checking screen that allows the user to check the captured ophthalmic image. Further, of the plurality of ophthalmic images, the CPU 23 may display the ophthalmic image having a high degree of divergence when the viewer for displaying the captured ophthalmic image is activated. In this case, the user can easily check the ophthalmic image obtained by imaging the part having a high degree of abnormality in the structure. This processing can be similarly executed when the ophthalmic image capturing device 11B executes the ophthalmic image processing.

Further, when the ophthalmic image capturing device 11B executes the ophthalmic image processing, the CPU 13B of the ophthalmic image capturing device 11B outputs the imaging instruction for capturing an image (in the second embodiment, at least one of the two-dimensional tomographic image, the three-dimensional tomographic image, the motion contrast image, or the like) of the part having the degree of divergence equal to or higher than the threshold value (S25). Note that the CPU 13B may capture the ophthalmic image of the same part a plurality of times and acquire an average added image of the plurality of captured ophthalmic images when capturing an image of the part having the degree of divergence equal to or higher than the threshold value. In this case, the ophthalmic image of the part having a high degree of abnormality in the structure is acquired with high quality. Further, the ophthalmic image processing device 23 may output the imaging instruction to the ophthalmic image capturing device 11B.

Next, the CPU 23 executes follow-up processing (S46). The follow-up processing is processing of allowing the user to perform a follow up of the subject eye. As described above, the acquired degree of divergence is stored in the storage device 24 (S39). In the follow-up processing, the CPU 23 displays a plurality of degrees of divergence for each of the plurality of ophthalmic images obtained by capturing the same tissue of the subject eye at different times on the display device 28. Therefore, the user can appropriately recognize the progress of the abnormality in the structure and the like by comparing the plurality of degrees of divergence. Note that the CPU 23 may display a plurality of values of the degree of divergence (for example, the degree of divergence table 53), may display a plurality of degrees of structural abnormality graphs 52, and may display a plurality of degrees of structural abnormality maps 55.

Next, the CPU 23 generates image quality evaluation information for evaluating the image quality of the ophthalmic image based on the degree of divergence acquired for the ophthalmic image (S47). The degree of divergence may also be high when the image quality of the ophthalmic image is poor. Therefore, the image quality of the ophthalmic image can be appropriately recognized by generating the image quality evaluation information based on the degree of divergence. The specific method for generating the image quality evaluation information can be appropriately selected. As an example, in the second embodiment, the CPU 23 acquires the strength of the signal of the ophthalmic image or an index (for example, SSI (Signal Strength Index) or QI (Quality Index), or the like) indicating the goodness of the signal. The CPU 23 generates the image quality evaluation information indicating that the image quality is poor when the acquired index is equal to or less than the threshold value and the average value of the degree of divergence is equal to or higher than the threshold value. Further, the CPU 23 may generate the image quality evaluation information indicating that the image quality is poor when all the degree of divergence of each part of the ophthalmic image are high (for example, when all the degree of divergence of each part are equal to or higher than the threshold value). Further, at least one of the values of the degree of divergence itself, the degree of structural abnormality graph 52, and the degree of structural abnormality map 55 may be used as the image quality evaluation information.

The techniques disclosed in the above embodiments are merely examples. Therefore, it is possible to modify the techniques exemplified in the above embodiments. First, it is also possible to implement only some of the plurality of techniques exemplified in the above embodiments.

Figure 10:
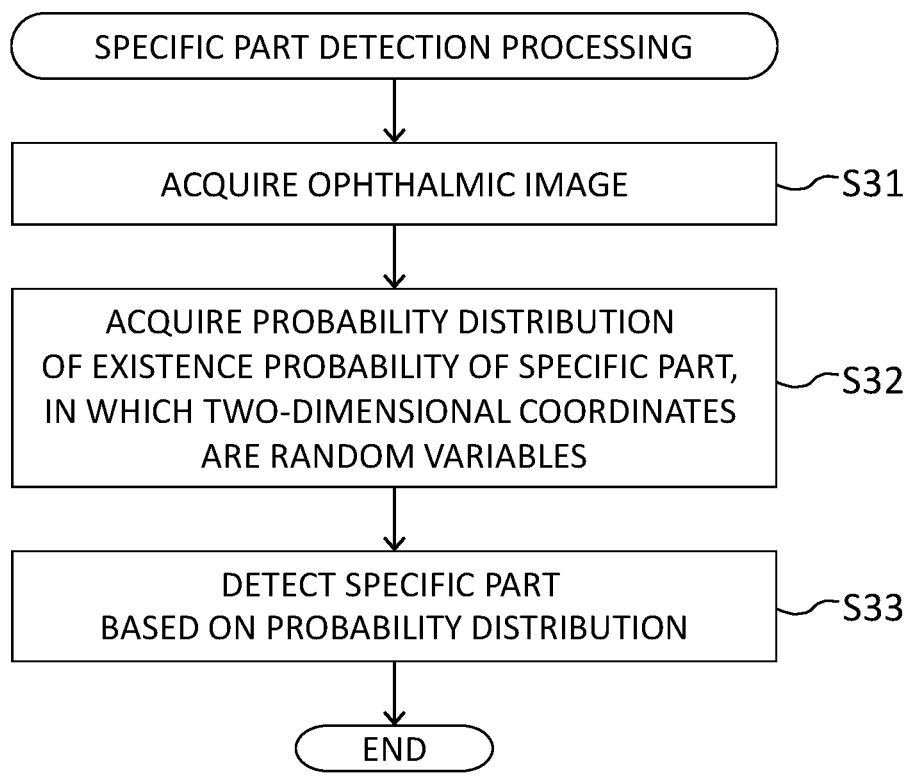
FIG. 10 is a flowchart of specific part detection processing executed by the ophthalmic image processing device 21.

For example, in the first embodiment, the ophthalmic image processing device 21 may execute only one of the boundary detection processing (see FIG. 5) and the specific part detection processing (see FIG. 10).

For example, in the second embodiment, the ophthalmic image processing device 21 may execute only the processing of acquiring the degree of divergence of the two-dimensional tomographic image (S31 to S40) and omit the processing of acquiring the degree of divergence of the entire three-dimensional tomographic image. In this case, the ophthalmic image acquired in S31 may be a two-dimensional tomographic image. Further, the ophthalmic image processing device 21 may use the degree of divergence as the image quality evaluation information without using the degree of divergence as the structural information indicating the degree of abnormality in the structure of the tissue.

Further, in the second embodiment, it is possible to change the method of using the acquired degree of divergence. For example, of the plurality of two-dimensional tomographic images that constitute the three-dimensional tomographic image, the CPU 23 may input the two-dimensional tomographic image having the highest degree of divergence or the two-dimensional tomographic image having the degree of divergence equal to or higher than the threshold value into the mathematical model that outputs an automatic diagnosis result related to the disease of the subject eye. This mathematical model is trained in advance by using the machine learning algorithm so that the automatic diagnosis result is output based on the input ophthalmic image. In this case, the efficient automatic diagnosis result can be obtained by using the two-dimensional tomographic image having a high degree of abnormality in the structure of the plurality of two-dimensional tomographic images that constitute the three-dimensional tomographic image.

Note that regarding the first aspect, the second aspect, and the third aspect, the processing of acquiring the training ophthalmic image in S1 in FIG. 2 is an example of an "input training data acquisition step". The processing of acquiring training data in S2 of FIG. 2 is an example of an "output training data acquisition step". The processing of training the mathematical model in S3 in FIG. 2 is an example of a "training step". The processing of acquiring the ophthalmic image in S11 in FIG. 5 and S31 in FIG. 10 is an example of an "image acquisition step". The processing of acquiring the probability distribution in S14 in FIG. 5 and S32 in FIG. 10 is an example of a "probability distribution acquisition step". The processing of detecting the boundary or the specific part in S16 and S24 in FIG. 5 and S33 in FIG. 10 is an example of a "detection step". The processing of acquiring the probability map in S15 in FIG. 5 is an example of a "map acquisition step". The processing of acquiring the Enface image in S25 in FIG. 5 is an example of an "Enface image acquisition step".

Figure 13:
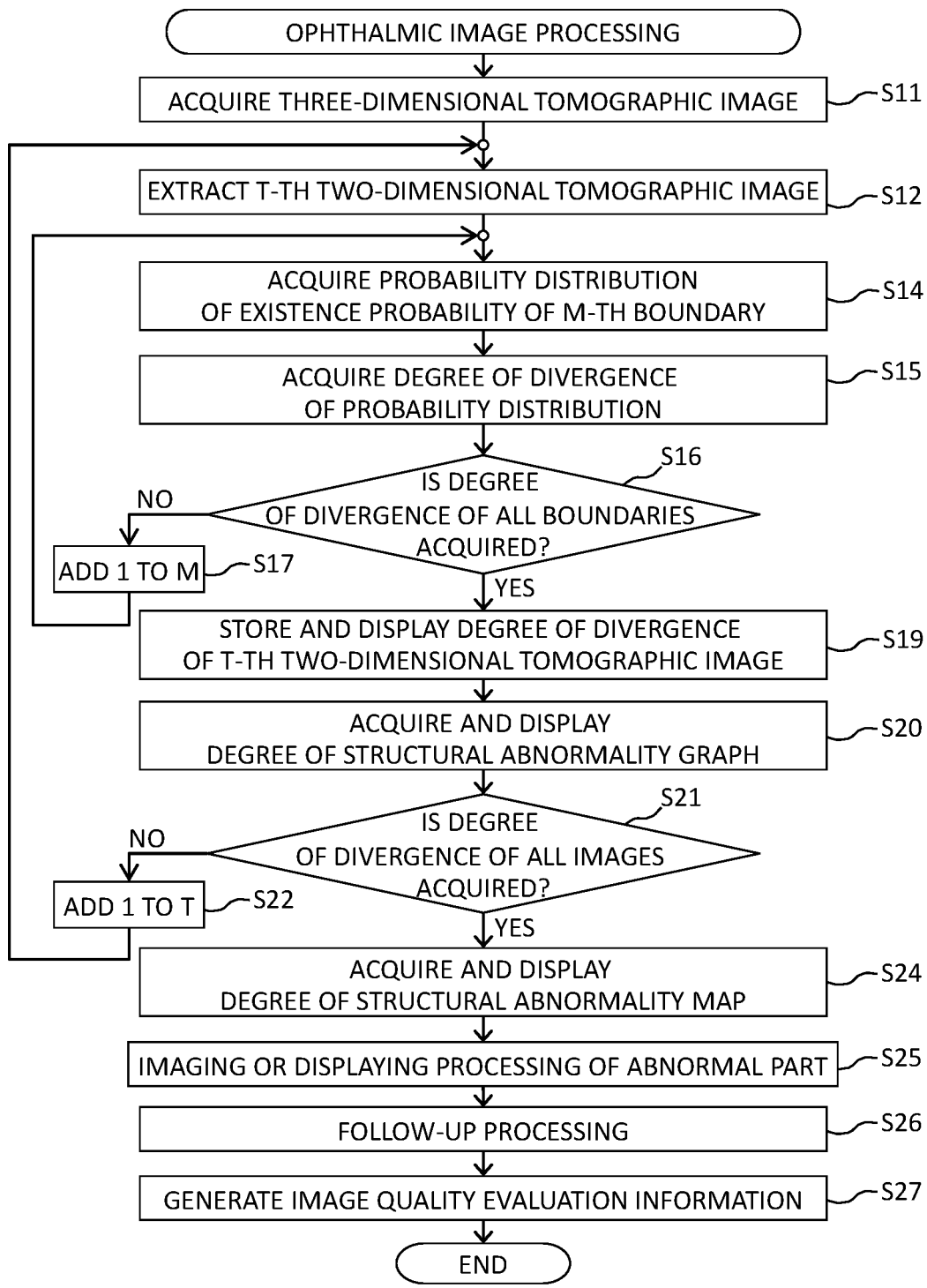
FIG. 13 is a flowchart of ophthalmic image processing according to a second embodiment, which is executed by the ophthalmic image processing device 21.

Regarding the fourth aspect, the fifth aspect, and the sixth aspect, the processing of acquiring the ophthalmic image in S21 in FIG. 13 is an example of an "image acquisition step". The processing of acquiring the probability distribution in S24 in FIG. 13 is an example of a "probability distribution acquisition step". The processing of acquiring the degree of divergence as structural information in S25 in FIG. 13 is an example of a "structural information acquisition step".

The invention claimed is:

1. An ophthalmic image processing device that processes an ophthalmic image which is an image of a tissue of a subject eye, comprising:
  a controller configured to:

acquire an ophthalmic image captured by an ophthalmic image capturing device;

acquire a probability distribution for identifying a tissue in the ophthalmic image by inputting the ophthalmic image into a mathematical model trained with using a machine learning algorithm; and acquire a degree of divergence of the acquired probability distribution with respect to the probability distribution acquired in a case where the tissue is accurately identified, as structural information indicating a degree of abnormality in a structure of the tissue.

2. The ophthalmic image processing device according to claim 1, wherein the mathematical model is trained with using a training data set in which data of an ophthalmic image of a tissue of a subject eye captured ago is used as an input side, and data indicating the tissue in the ophthalmic image on the input side is used as an output side.

3. The ophthalmic image processing device according to claim 1, wherein the degree of divergence includes an entropy of the acquired probability distribution.

4. The ophthalmic image processing device according to claim 1, wherein the ophthalmic image is a two-dimensional tomographic image or a three-dimensional tomographic image of the tissue, and the controller is configured to:

acquire the probability distribution for identifying one or more layers or boundaries included in a plurality of layers in the ophthalmic image and boundaries of the layers by inputting the ophthalmic image into the mathematical model; and acquire the degree of divergence for the one or more layers or boundaries.

5. The ophthalmic image processing device according to claim 1, wherein the controller acquires at least one of a graph and a map showing a magnitude of the degree of divergence with respect to a position in the tissue.

6. The ophthalmic image processing device according to claim 1, wherein the controller performs at least one of:

processing of outputting an imaging instruction for imaging a part having the degree of divergence equal to or higher than a threshold value in the tissue, to the ophthalmic image capturing device; and processing of displaying a tomographic image or an enlarged image of a part having the degree of divergence equal to or higher than a threshold value, on a display device.

7. The ophthalmic image processing device according to claim 1, wherein the controller is configured to:

store the acquired degree of divergence in a storage device; and display a plurality of the degrees of divergence related to each of a plurality of the ophthalmic images obtained by capturing an identical tissue of a subject eye at different times, on a display device.

8. The ophthalmic image processing device according to claim 1, wherein the controller is configured to generate image quality evaluation information used for evaluating image quality of the ophthalmic image, based on the acquired degree of divergence for the ophthalmic image.

9. An OCT device that captures an ophthalmic image of a tissue of a subject eye by processing an OCT signal derived from reference light and reflected light of measurement light with which the tissue is irradiated, comprising:

a controller configured to:

acquire a probability distribution for identifying a tissue in the ophthalmic image by inputting the captured ophthalmic image into a mathematical model trained with using a machine learning algorithm; and acquire a degree of divergence of the acquired probability distribution with respect to the probability distribution acquired in a case where the tissue is accurately identified, as structural information indicating a degree of abnormality in a structure of the tissue.

10. A non-transitory computer-readable storage medium storing an ophthalmic image processing program executed by an ophthalmic image processing device that processes an ophthalmic image which is an image of a tissue of a subject eye, the program being executed by a controller of the ophthalmic image processing device to cause the ophthalmic image processing device to execute:

an image acquisition step of acquiring an ophthalmic image captured by an ophthalmic image capturing device;

a probability distribution acquisition step of acquiring a probability distribution for identifying a tissue in the ophthalmic image by inputting the ophthalmic image into a mathematical model trained with using a machine learning algorithm; and a structural information acquisition step of acquiring a degree of divergence of the acquired probability distribution with respect to the probability distribution acquired in a case where the tissue is accurately identified, as structural information indicating a degree of abnormality in a structure of the tissue.

* * * * *